US012758708B2

(12) United States Patent
Jezek et al.

(10) Patent No.: US 12,758,708 B2
(45) **Date of Patent: *Oct. 13, 2026**

(54) MEDICAL INFUSION PUMP SYSTEM FOR THE DELIVERY OF AN INSULIN COMPOUND

(71) Applicant: ARECOR LIMITED, Saffron Walden (GB)

(72) Inventors: Jan Jezek, Saffron Walden (GB); David Gerring, Saffron Walden (GB); Sarah Howell, Saffron Walden (GB); Leon Zakrzewski, Saffron Walden (GB)

(73) Assignee: Arecor Limited, Saffron Walden (GB)

( * ) Notice: Subject to any disclaimer, the term of this patent is extended or adjusted under 35 U.S.C. 154(b) by 1504 days.

This patent is subject to a terminal disclaimer.

(21) Appl. No.: 17/044,729

(22) PCT Filed: Apr. 4, 2019

(86) PCT No.: PCT/GB2019/050988
§ 371 (c)(1),
(2) Date: Oct. 1, 2020

(87) PCT Pub. No.: WO2019/193351
PCT Pub. Date: Oct. 10, 2019

(65) Prior Publication Data

US 2021/0113763 A1 Apr. 22, 2021

(30) Foreign Application Priority Data

Apr. 4, 2018 (GB) ..................................... 1805536
May 3, 2018 (GB) ..................................... 1807320

(51) Int. Cl.

| | |
|---|---|
| ***A61M 5/168*** | (2006.01) |
| ***A61K 9/00*** | (2006.01) |
| ***A61K 31/465*** | (2006.01) |
| ***A61K 33/30*** | (2006.01) |
| ***A61K 38/28*** | (2006.01) |
| ***A61K 47/02*** | (2006.01) |
| ***A61K 47/10*** | (2017.01) |
| ***A61K 47/12*** | (2006.01) |
| ***A61K 47/26*** | (2006.01) |
| ***A61M 5/142*** | (2006.01) |
| *A61K 47/18* | (2017.01) |
| *A61K 47/22* | (2006.01) |

(52) U.S. Cl.
CPC ....... *A61M 5/16804* (2013.01); *A61K 9/0019* (2013.01); *A61K 31/465* (2013.01); *A61K 33/30* (2013.01); *A61K 38/28* (2013.01); *A61K 47/02* (2013.01); *A61K 47/10* (2013.01); *A61K 47/12* (2013.01); *A61K 47/26* (2013.01); *A61M 5/14248* (2013.01); *A61M 5/14276* (2013.01); *A61K 47/18* (2013.01); *A61K 47/22* (2013.01)

(58) Field of Classification Search
None
See application file for complete search history.

(56) References Cited

U.S. PATENT DOCUMENTS

| | | | | |
|---|---|---|---|---|
| 5,866,538 | A | 2/1999 | Norup et al. | |
| 6,960,561 | B2 | 11/2005 | Boderke | |
| 7,205,276 | B2 | 4/2007 | Boderke | |
| 7,279,457 | B2 | 10/2007 | Pohl et al. | |
| 7,452,860 | B2 | 11/2008 | Boderke | |
| 7,476,652 | B2 | 1/2009 | Brunner-Schwarz et al. | |
| 7,696,162 | B2 | 4/2010 | Boderke | |
| 7,998,927 | B2 | 8/2011 | Maggio | |
| 8,318,154 | B2 | 11/2012 | Frost et al. | |
| 8,324,157 | B2 | 12/2012 | Olsen et al. | |
| 8,772,231 | B2 | 7/2014 | Maggio | |
| 11,278,624 | B2 * | 3/2022 | Gerring | A61K 47/183 |
| 2005/0214251 | A1 | 9/2005 | Pohl et al. | |
| 2008/0039365 | A1 | 2/2008 | Steiner et al. | |
| 2008/0194461 | A1 | 8/2008 | Maggio | |
| 2008/0268032 | A1 | 10/2008 | Maggio | |
| 2009/0011976 | A1 | 1/2009 | Ludvigsen et al. | |
| 2009/0137455 | A1 | 5/2009 | Steiner et al. | |
| 2010/0210506 | A1 | 8/2010 | Quay et al. | |
| 2010/0227795 | A1 | 9/2010 | Steiner et al. | |
| 2012/0035103 | A1 * | 2/2012 | Pillion | A61K 38/28 514/6.3 |

(Continued)

FOREIGN PATENT DOCUMENTS

| | | | |
|---|---|---|---|
| EP | 0214826 | A2 | 3/1987 |
| EP | 0375437 | A2 | 6/1990 |

(Continued)

OTHER PUBLICATIONS

Maggio (J. Excipients and Food Chem., 2012, 3(2), 45-53) (Year: 2012).*

(Continued)

*Primary Examiner* — Brian Gangle
*Assistant Examiner* — Andrea K Mccollum
(74) *Attorney, Agent, or Firm* — Nixon & Vanderhye P.C.

(57) ABSTRACT

Provided herein is a medical infusion pump system that contains a pump and a reservoir containing an aqueous liquid pharmaceutical composition that is delivered to a subject by the pump and that contains an insulin compound at a concentration of 400 U/mL or more, ionic zinc and a non-ionic surfactant, and wherein the pump delivers the composition in pulses wherein the volume of the pulse is 0.5 μL or less.

48 Claims, 2 Drawing Sheets

Figure 1:
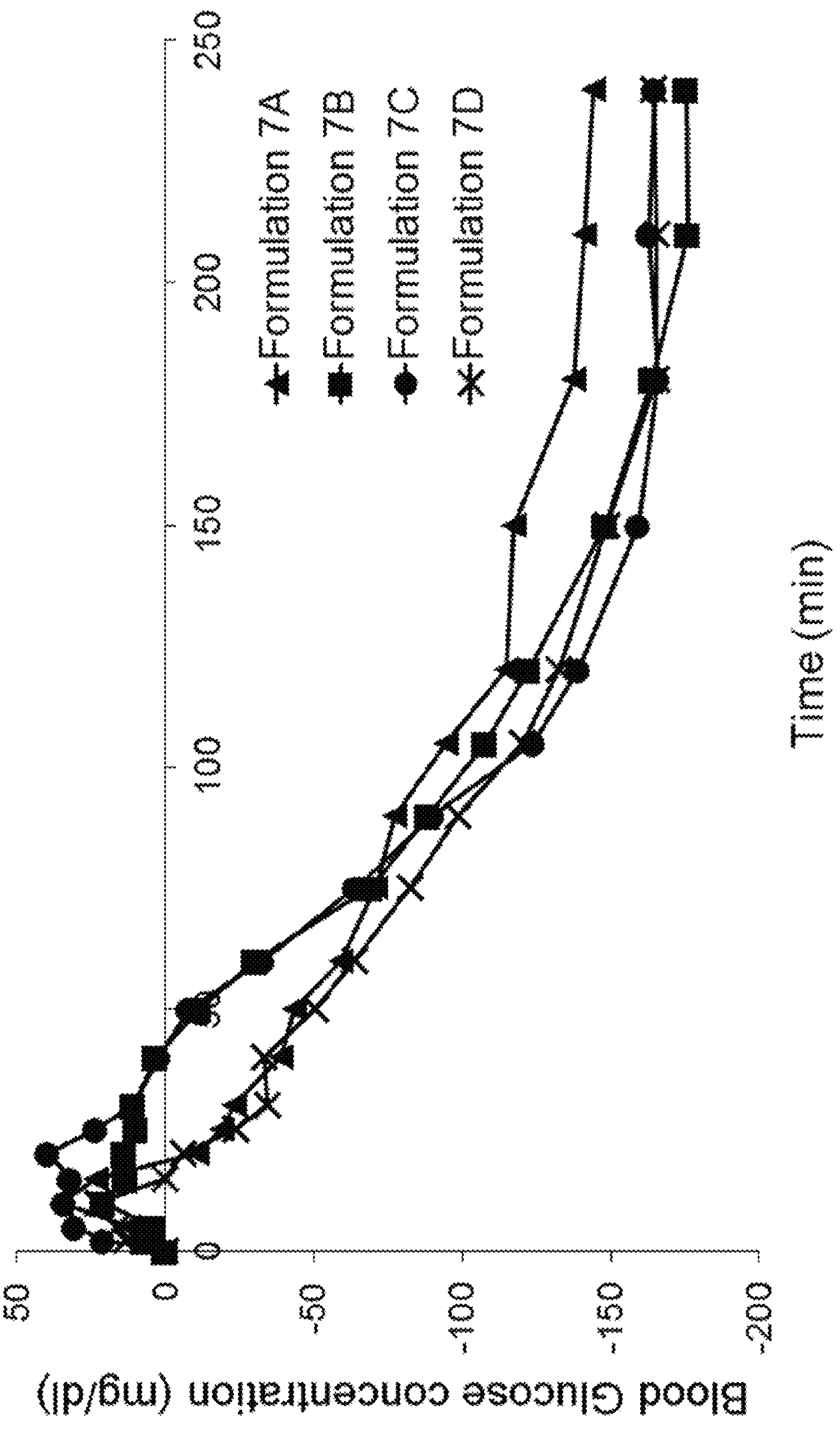

Specification includes a Sequence Listing.

(56) References Cited

U.S. PATENT DOCUMENTS

| | | | |
|---|---|---|---|
| 2012/0178675 A1 | 7/2012 | Pohl et al. | |
| 2013/0231281 A1 | 9/2013 | Soula et al. | |
| 2013/0302275 A1 | 11/2013 | Wei et al. | |
| 2013/0331320 A1 | 12/2013 | Havelund et al. | |
| 2014/0024582 A1 | 1/2014 | Yang | |
| 2014/0135263 A1 | 5/2014 | Pohl et al. | |
| 2014/0142034 A1 | 5/2014 | Soula et al. | |
| 2014/0221285 A1 | 8/2014 | Bley et al. | |
| 2014/0357554 A1 | 12/2014 | Pohl et al. | |
| 2015/0190475 A1 | 7/2015 | Bley et al. | |
| 2015/0265683 A1 | 9/2015 | Sahib et al. | |
| 2015/0273022 A1 | 10/2015 | Wilson et al. | |
| 2016/0015814 A1 | 1/2016 | Soula et al. | |
| 2016/0082106 A1 | 3/2016 | Soula et al. | |
| 2016/0166695 A1* | 6/2016 | Akers | A61P 3/10 514/5.9 |
| 2017/0056478 A1 | 3/2017 | Akers et al. | |
| 2018/0078645 A1* | 3/2018 | Gerring | A61K 47/10 |

FOREIGN PATENT DOCUMENTS

| | | | |
|---|---|---|---|
| EP | 0678522 A1 | 10/1995 | |
| EP | 1283051 A1 | 2/2003 | |
| EP | 1381385 B1 | 1/2004 | |
| EP | 1740154 B1 | 1/2007 | |
| EP | 2106790 B1 | 10/2009 | |
| EP | 2289539 B1 | 3/2011 | |
| EP | 2319500 B1 | 5/2011 | |
| EP | 2340033 B1 | 7/2011 | |
| WO | WO1991/09617 A1 | 7/1991 | |
| WO | WO1996/10417 A1 | 4/1996 | |
| WO | WO1997/17945 A2 | 5/1997 | |
| WO | WO1999/34821 A1 | 7/1999 | |
| WO | WO2002/076495 A1 | 10/2002 | |
| WO | WO2005/089722 A1 | 9/2005 | |
| WO | WO2007/041481 A1 | 4/2007 | |
| WO | WO2007/121256 A2 | 10/2007 | |
| WO | WO2007/149096 A1 | 12/2007 | |
| WO | WO2008/084237 A2 | 7/2008 | |
| WO | WO2010/102020 A1 | 9/2010 | |
| WO | WO2010/115819 A1 | 10/2010 | |
| WO | WO2010/149772 A1 | 12/2010 | |
| WO | WO2011/094632 A1 | 8/2011 | |
| WO | WO2012/006283 A1 | 1/2012 | |
| WO | WO2013/021143 A1 | 2/2013 | |
| WO | WO2013/158618 A1 | 10/2013 | |
| WO | WO2013/186138 A1 | 12/2013 | |
| WO | WO2014/096985 A2 | 6/2014 | |
| WO | WO2015/059302 A1 | 4/2015 | |
| WO | WO2015/114374 A1 | 8/2015 | |
| WO | WO2015/120457 A1 | 8/2015 | |
| WO | WO2015/171484 A1 | 11/2015 | |
| WO | WO2016/100042 A1 | 6/2016 | |
| WO | WO-2017191464 A1 * | 11/2017 | A61K 33/30 |
| WO | WO2018/060735 A1 | 4/2018 | |
| WO | WO2018/060736 A1 | 4/2018 | |
| WO | WO2018/203059 A1 | 11/2018 | |
| WO | WO2018/203060 A2 | 11/2018 | |
| WO | WO2018/203061 A1 | 11/2018 | |
| WO | WO2019/193349 A1 | 10/2019 | |
| WO | WO2019/193351 A1 | 10/2019 | |
| WO | WO2019/193353 A1 | 10/2019 | |

OTHER PUBLICATIONS

SSED for MiniMed 670G system (published Sep. 28, 2016; downloaded from https://www.accessdata.fda.gov/cdrh_docs/pdf16/p160017b.pdf). (Year: 2016).*

De la Peña et al. "Pharmacokinetics and Pharmacodynamics of High-Dose Human Regular U-500 Insulin Versus Human Regular U-100 Insulin in Healthy Obese Subjects", Diabetes Care, 2011, 34, pp. 2496-2501.

Lougheed et al., "Physical stability of insulin formulations" Diabetes, American Diabetes Association, 1983, vol. 32, No. 5, pp. 424-432.

Moghaddam et al., "Evaluation of Insulin Stability in the Presence of Nonionic Surface Active Agents (Polysorbate Groups) by Circular Dichroism and Fluorescence Spectroscopy" Asian Journal of Biochemistry, 2015, vol. 10, No. 1, pp. 17-30.

Pohl et al. "Ultra-Rapid Absorption of Recombinant Human Insulin Induced by Zinc Chelation and Surface Charge Masking", Journal of Diabetes Science and Technology, 2012, vol. 6, No. 4, pp. 755-763.

Steiner S et al. "A novel insulin formulation with a more rapid onset of action" Diabetologia; Clinical & Experimental Diabetes & Metabolism, 2008, vol. 51, No. 9, pp. 1602-1606.

Pillai et al. "Transdermal iontophoresis of insulin II. Physicochemical considerations" International Journal of Pharmaceutics, 2003, vol. 254, pp. 271-280.

Liu et al. "Insulin Aggregation in Aqueous Media and Its Effect on Alpha-Chymotrypsin-Mediated Proteolytic Degradation" Pharmaceutical Research, 1991, vol. 8, No. 7, pp. 925-929.

Prabhu et al. "A study of factors controlling dissolution kinetics of zinc complexed protein suspensions in various ionic species" International Journal of Pharmaceutics 2001, vol. 217, pp. 71-78.

Arnebrant et al. "Adsorption of Insulin on Metal Surfaces in Relation to Association Behavior" Journal of Colloid and Interface Science, 1988, vol. 122, No. 2, pp. 557-566.

Okada et al. "Vaginal Absorption of a Potent Luteinizing Hormone-Releasing Hormone Analogue (Leuprolide) in Rats 11: Mechanism of Absorption Enhancement with Organic Acids" Journal of Pharmaceutical Sciences, 1983, vol. 72, No. 1, pp. 75-78.

Rifkin, R. A., et al., "n-Dodecyl-B-D-Maltoside Inhibits Aggregation of Human Interferon-β-1b and Reduces Its Immunogenicity," J Neuroimmune Pharmacol., 6:158-162 (2011).

* cited by examiner

SEQUENCE LISTING

<160> NUMBER OF SEQ ID NOS: 5

<210> SEQ ID NO 1
<211> LENGTH: 21
<212> TYPE: PRT
<213> ORGANISM: Homo sapiens

<400> SEQUENCE: 1

```
Gly Ile Val Glu Gln Cys Cys Thr Ser Ile Cys Ser Leu Tyr Gln Leu
1               5                   10                  15

Glu Asn Tyr Cys Asn
            20
```

<210> SEQ ID NO 2
<211> LENGTH: 30
<212> TYPE: PRT
<213> ORGANISM: Homo sapiens

<400> SEQUENCE: 2

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

<210> SEQ ID NO 3
<211> LENGTH: 30
<212> TYPE: PRT
<213> ORGANISM: Artificial sequence
<220> FEATURE:
<223> OTHER INFORMATION: B chain of insulin lispro

<400> SEQUENCE: 3

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30
```

<210> SEQ ID NO 4
<211> LENGTH: 30
<212> TYPE: PRT
<213> ORGANISM: Artificial sequence
<220> FEATURE:
<223> OTHER INFORMATION: B chain of insulin aspart

<400> SEQUENCE: 4

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30
```

<210> SEQ ID NO 5
<211> LENGTH: 30
<212> TYPE: PRT
<213> ORGANISM: Artificial sequence
<220> FEATURE:
<223> OTHER INFORMATION: B chain of insulin glulisine

<400> SEQUENCE: 5

```
Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30
```

MEDICAL INFUSION PUMP SYSTEM FOR THE DELIVERY OF AN INSULIN COMPOUND

CROSS-REFERENCE TO RELATED APPLICATIONS

This application is the U.S. national phase of International Application No. PCT/GB2019/050988 filed Apr. 4, 2019 which designated the U.S. and claims priority to GB 1805536.8 filed Apr. 4, 2018 and GB 1807320.5 filed May 3, 2018, the entire contents of each of which are hereby incorporated by reference.

REFERENCE TO SEQUENCE LISTING SUBMITTED ELECTRONICALLY

The content of the electronically submitted sequence listing (Name: 6662_1320_Sequence_Listing.txt; Size: 2,086 bytes; and Date of Creation: Jul. 29, 2026) is incorporated herein by reference in its entirety.

FIELD OF THE INVENTION

This invention relates inter alia to a medical infusion pump system for the delivery of an insulin compound in a high strength composition, particularly a high strength rapid acting aqueous liquid pharmaceutical composition of insulin or an insulin analogue. Such a system is suitable for the treatment of subjects suffering from diabetes mellitus, especially Type 1 diabetes mellitus.

BACKGROUND OF THE INVENTION

Diabetes mellitus ("diabetes") is a metabolic disorder associated with poor control of blood sugar levels leading to hypo or hyperglycaemia. Untreated diabetes can lead to serious microvascular and macrovascular complications including coronary artery disease, peripheral artery disease, stroke, diabetic nephropathy, neuropathy and retinopathy. The two main types of diabetes are (i) Type 1 diabetes resulting from the pancreas not producing insulin for which the usual treatment is insulin replacement therapy and (ii) Type 2 diabetes where patients either produce insufficient insulin or have insulin resistance and for which treatments include insulin sensitising agents (such as metformin or pioglitazone), traditional insulin secretagogues (such as sulfonylureas), SGLT2 inhibitors (such as dapagliflozin, canagliflozin and empagliflozin) which reduce glucose absorption in the kidneys and so promote glucose excretion, GLP-1 agonists (such as exenatide and dulaglutide) which stimulate insulin release from pancreatic beta cells and DPPIV inhibitors (such as sitagliptin or vildagliptin) which inhibit breakdown of GLP-1 leading to increased insulin secretion. Patients with Type 2 diabetes may eventually require insulin replacement therapy.

For patients requiring insulin replacement therapy, a range of therapeutic options are possible. The use of recombinant human insulin has in recent times been overtaken by use of insulin analogues which have modified properties, for example, are longer acting or faster acting than normal insulin. Thus, a common regimen for a patient involves receiving a long acting basal insulin supplemented by a rapid acting insulin around mealtimes.

Insulin is a peptide hormone formed of two chains (A chain and B chain, respectively 21 and 30 amino acids in length) linked via disulfide bridges. Insulin normally exists at neutral pH in the form of a hexamer, each hexamer comprising three dimers bound together by zinc ions. Histidine residues on the insulin are known to be involved in the interaction with the zinc ions. Insulin is stored in the body in the hexameric form but the monomer form is the active form. Traditionally, therapeutic compositions of insulin have also been formulated in hexameric form in the presence of zinc ions. Typically, there are approximately three zinc cations per one insulin hexamer. It has been appreciated that the hexameric form is absorbed from the injection site considerably more slowly than the monomeric and dimeric forms. Therefore, a faster onset of insulin action can be achieved if the hexameric form is destabilised allowing a more rapid dissociation of the zinc-bound hexamer into dimers and monomers in the subcutaneous space following injection. Three insulin analogues have been genetically engineered with this principle in mind. A first is insulin lispro (HUMALOG®) in which residues 28 and 29 of the B chain (Pro and Lys respectively) are reversed, a second is insulin aspart (NOVORAPID®) in which residue 28 of the B chain, normally Pro, is replaced by Asp, and a third is insulin glulisine (APIDRA®) in which residue 3 of the B chain, normally Asn is replaced by Lys and residue 29 of the B chain, normally Lys, is replaced by Glu.

Whilst the existing rapid acting insulin analogues can achieve a more rapid onset of action, it has been appreciated that even more rapid acting ("ultra rapid acting") insulins can be achieved by removing the zinc cations from insulin altogether. Unfortunately, the consequence of the hexamer dissociation is typically a considerable impairment in insulin stability both with respect to physical stability (e.g. stability to aggregation) and chemical stability (e.g. stability to deamidation). For example, monomeric insulin or insulin analogues having a rapid onset of action are known to aggregate and become physically unstable very rapidly because the formation of insoluble aggregates proceeds via monomers of insulin. Various approaches to addressing this problem have been described in the art:

U.S. Pat. No. 5,866,538 (Norup) describes insulin preparations of superior chemical stability comprising human insulin or an analogue or derivative thereof, glycerol and/or mannitol and 5 mM to 100 mM of a halogenide (e.g. NaCl).

U.S. Pat. No. 7,205,276 (Boderke) addresses the stability problems associated with preparing zinc-free formulations of insulin and insulin derivatives and analogues and describes an aqueous liquid formulation comprising at least one insulin derivative, at least one surfactant, optionally at least one preservative and optionally at least one of an isotonicizing agent, a buffer and an excipient, wherein the formulation is stable and free from or contains less than 0.4% (e.g. less than 0.2%) by weight of zinc based on the insulin content of the formulation. The preferred surfactant appears to be polysorbate 20 (polyoxyethylene (20) sorbitan monolaurate).

US2008/0194461 (Maggio) describes formulations of peptides and polypeptides including insulin which contain an alkyl glycoside, which component is said to reduce aggregation and immunogenicity.

WO2012/006283 (Pohl) describes formulations containing insulin together with a zinc chelator such as ethylenediaminetetraacetate (EDTA). Modulating the type and quantity of EDTA is said to change the insulin absorption profile. Calcium EDTA is the preferred form of EDTA since it is said to be associated with reduced pain at the injection site and is less likely to remove calcium from the body. Preferred formulations also contain citrate which is said to further enhance absorption and to improve the chemical stability of the formulation.

US2010/0227795 (Steiner) describes a composition comprising insulin, a dissociating agent such as citric acid or sodium citrate, and a zinc chelator such as EDTA wherein the formulation has a physiological pH and is a clear aqueous solution. The formulations are said to have improved stability and rapid onset of action.

WO2015/120457 (Wilson) describes stabilized ultra-rapid acting insulin formulations comprising insulin in combination with a zinc chelator such as EDTA, a dissolution/stabilization agent such as citric acid, a magnesium salt, a zinc compound and optionally additional excipients.

Further approaches to accelerating the absorption and effect of insulin through the use of specific accelerating additives have been described:

WO91/09617 (Jorgensen) reports that nicotinamide or nicotinic acid or a salt thereof increases the speed of absorption of insulin from aqueous preparations administered parenterally.

WO2010/149772 (Olsen) describes a formulation comprising insulin, a nicotinic compound and arginine. The presence of arginine is said to improve the chemical stability of the formulation.

WO2015/171484 (Christe) describes rapid-acting formulations of insulin wherein onset of action and/or absorption of insulin is faster due to the presence of treprostinil.

US2013/0231281 (Soula) describes an aqueous solution composition comprising insulin or an insulin analogue and at least one oligosaccharide whose average degree of polymerisation is between 3 and 13 and whose polydispersity index is above 1.0, said oligosaccharide having partially substituted carboxyl functional groups, the unsubstituted carboxyl functional groups being salifiable. Such a formulation is said to be rapid acting.

WO2017/191464 (Arecor Limited) describes an aqueous liquid pharmaceutical formulation comprising insulin or an insulin analogue, ionic zinc, a chelating agent and polysorbate 80.

WO2016/100042 (Eli Lilly and Company) describes a composition of human insulin or insulin analogue that includes specific concentrations of citrate, chloride, in some cases including the addition of sodium chloride, zinc and, optionally magnesium chloride and/or surfactant, said to have faster pharmacokinetic and/or pharmacodynamic action than commercial formulations of existing insulin analogue products.

There are a number of devices that can be used to deliver insulin, including syringes, insulin pens and insulin pumps.

Syringes can typically be used to deliver basal (long-acting) insulins, typically as one injection per day. Whilst syringes are still used, they are gradually being replaced by more convenient insulin pens.

Insulin pens are a very convenient way of delivering both basal and prandial insulin. Insulin pens contain a cartridge that is filled with insulin and an apparatus for dispensing a required amount of insulin, as needed by the user. The required amount is first selected (this often referred to as being "dialed") using a specifically designed mechanism and then dispensed via a very small retractable needle whilst holding the pen against the body (typically the abdomen).

Insulin pumps represent the most advanced delivery system for insulin and are becoming increasingly popular. Insulin pumps have traditionally been used primarily by people with Type 1 diabetes, but they are also slowly becoming a treatment of choice for Type 2 diabetes. All insulin pumps comprise a reservoir in which an aqueous insulin composition is held and a pumping mechanism that dispenses the insulin composition subcutaneously into the body via a fine cannula, either as a bolus dose or as a continuous infusion.

Currently, there are three main categories of insulin pumps, traditional "tethered pumps", "patch pumps" and "implantable pumps".

A traditional tethered pump is worn in a pocket or clipped to a belt and uses a fine tubing to connect the pump to the cannula. The pump body contains buttons that allow programming the insulin delivery at a slow, continuous (basal) rate as well as in supplemental (bolus) doses before meals or suspending the insulin infusion, if necessary. Examples of traditional tethered pumps include MINIMED® 530G, MINIMED® 630G, MINIMED® 670G (Medtronic Diabetes).

A patch pump is worn directly on the body (typically the abdomen), attached via an adhesive layer. Patch pumps are controlled wirelessly by a separate device that allows programming the insulin delivery at a slow, continuous (basal) rate as well as in supplemental (bolus) doses before meals or suspending the insulin infusion, if necessary. The cannula is an inherent part of the patch pump, so no additional tubing is necessary. The cannula is inserted automatically after attaching the patch on the skin by programming the activation of the patch from a remote device. Examples of insulin patch pumps include OMNIPOD® (Insulet Corporation), T-SLIM® X2 (Tandem Diabetes Care), T-FLEX® (Tandem Diabetes Care), CELLNOVO® (Cellnovo)

Implantable insulin pumps are extremely rare, with <500 users world-wide. The pump is surgically implanted under the skin and a catheter from the pump extends into the peritoneal cavity. Delivery into the peritoneal cavity ensures a rapid delivery of insulin to the liver which is the normal target for insulin. The pump contains a reservoir in which the insulin composition is held and a mechanism for dispensing the composition at a required rate. The reservoir is re-fillable using a syringe via a specifically designed port. An example of an implantable insulin pump is the MINIMED® Implantable Pump (MIP) model 2000 (Medtronic Diabetes).

Many pumps are now available that work in conjunction with continuous glucose monitors that can alert the user to high or low blood glucose levels.

Commercially available rapid-acting insulin formulations are available as 100 U/ml formulations (HUMALOG® (insulin lispro), NOVORAPID® (also known as NOVOLOG®, insulin aspart) and APIDRA® (insulin glulisine)) and 200 U/ml formulations (HUMALOG®). Regular human insulin products are available as 100 U/ml formulations (e.g. HUMULIN® R) and a 500 U/ml formulation HUMULIN® R U-500). However, a considerable disadvantage of the regular human insulin is a slow onset of action compared with the rapid acting analogues. The speed of onset of action is further reduced at the higher concentration, making such concentrated insulin unsuitable for prandial use.

Compositions having a higher concentration of insulin compound are desirable e.g. for patients that require higher insulin doses, such as obese patients or patients who have developed insulin resistance. Compositions having a higher concentration of insulin are thus desirable for these categories of patients as the required high dose can be delivered in a smaller volume. Whilst the development of the 200 U/ml HUMALOG® formulation was an important step toward patient convenience in the situations described above, there remains a strong need to develop formulations of rapid-acting insulins at considerably higher concentrations, such as 400 U/ml or more or 500 U/ml or more or 1000 U/ml or more. It would also be advantageous to maintaining the rapid onset of action in such high strength compositions.

Compositions having a higher concentration of insulin compound are also highly desirable for miniaturization of delivery devices, particularly of insulin patch pumps. The ability to keep a given dose in a small volume means that the patch pump can be smaller and thus more convenient for the user. In addition, concentrated insulin compositions may allow longer use of the reservoir in the pump due to higher number of insulin units being held in a given volume.

A known problem associated with the use of formulations containing higher concentrations of insulin compound, in particular rapid-acting insulin compounds, is that the rapid-acting effects observed at low concentration (or low strength) formulations e.g. 100 U/ml of insulin compound, are reduced. Thus, increasing the concentration of insulin compound has been observed to lead to a slower onset of action even if the same dose is delivered, see for example de la Peña et al. Pharmacokinetics and Pharmacodynamics of High-Dose Human Regular U-500 Insulin Versus Human Regular U-100 Insulin in Healthy Obese Subjects, Diabetes Care, 34, pp 2496-2501, 2011.

A known problem associated with the use of insulin pumps is an occlusion, i.e. a blockage (e.g. of the cannula, the tubing or any other part of the microfluidic system that delivers insulin from the reservoir to the injection site. The occlusion may be caused by a number of factors, but is most commonly associated with insulin aggregation and consequent formation of insoluble particles. Avoidance of the risk of an occlusion leading to failure of a pump is a prerequisite for successful development of an autonomous insulin pump system, especially one which is to be implanted.

It would be desirable if a medical infusion pump system were available which can deliver compositions of insulin or insulin analogues from a reservoir at high concentration, which are rapid or ultra-rapid acting, and which remain stable upon storage and in-use at temperatures both inside and outside the body. In addition, in order to improve the convenience of use of such medical infusion pump systems it would be desirable to reduce the size of the system which would require reduction of size of the reservoir and consequent need to increase the concentration of insulin so that the total amount of insulin in the reservoir remains the same.

SUMMARY OF THE INVENTION

According to the invention there is provided a medical infusion pump system comprising a medical infusion pump and a reservoir comprising an aqueous liquid pharmaceutical composition for delivery by means of said pump to a mammal wherein the composition comprises (i) an insulin compound at a concentration of 400 U/mL or more, (ii) ionic zinc and (iii) a non-ionic surfactant and wherein the said pump delivers the composition in pulses wherein the volume of the pulse is 0.5 μL or less. Suitably, the composition of the system of the invention is of low ionic strength e.g. the ionic strength of the composition is less than 40 mM, calculated using formula I as described herein.

The compositions of the system of the invention provide insulin in a form with good physical and chemical stability, preferably in a form which is rapid or ultra-rapid acting. The compositions have a high concentration (or "high strength") of insulin compound i.e. 400 U/ml or more. The present inventors have importantly identified that use of a non-ionic surfactant increases the storage stability of insulin compositions, particularly high strength compositions, which is expected to permit the use of a pump system to deliver aqueous liquid pharmaceutical compositions of insulin to the body of a mammal from one or more reservoirs with good in-use stability.

As noted in the background discussion above, use of EDTA to chelate zinc ions in hexameric insulin does increase the rapidity of action but at the cost of greatly reduced stability. Without being limited by theory, the present inventors have also appreciated that the use in certain embodiments of the invention of zinc together with species which bind zinc less strongly can achieve similar effects in terms of speed of action and their moderately destabilising effects can be reduced or eliminated by using a non-ionic surfactant. The present inventors have further appreciated that the presence of such a zinc binding species accelerates the onset of action of a high concentration (high strength) insulin compound composition thereby mitigating the delaying effect on insulin onset of action which has been observed when the concentration of insulin compound in a composition is increased.

Compositions of the system of the invention may be used in the treatment of subjects suffering from diabetes mellitus, particularly Type 1 diabetes mellitus.

As can be seen from the accompanying examples, example compositions of the system of the invention are significantly more stable than compositions without non-ionic surfactant including under stress conditions that model those of an infusion pump system. The example compositions achieve a rapid speed of action of insulin and are more stable than prior art rapid acting insulin compositions containing EDTA. Furthermore, example compositions of the system of the invention contain high concentrations of insulin compound while maintaining a rapid onset of action.

Description of the Sequence Listing

SEQ ID NO: 1: A chain of human insulin
SEQ ID NO: 2: B chain of human insulin
SEQ ID NO: 3: B chain of insulin lispro
SEQ ID NO: 4: B chain of insulin aspart
SEQ ID NO: 5: B chain of insulin glulisine

FIGURES

FIG. 1. Pharmacodynamic profiles of compositions 7A-7D of Example 7 in a validated diabetic Yucatan miniature pig model.

Figure 2:
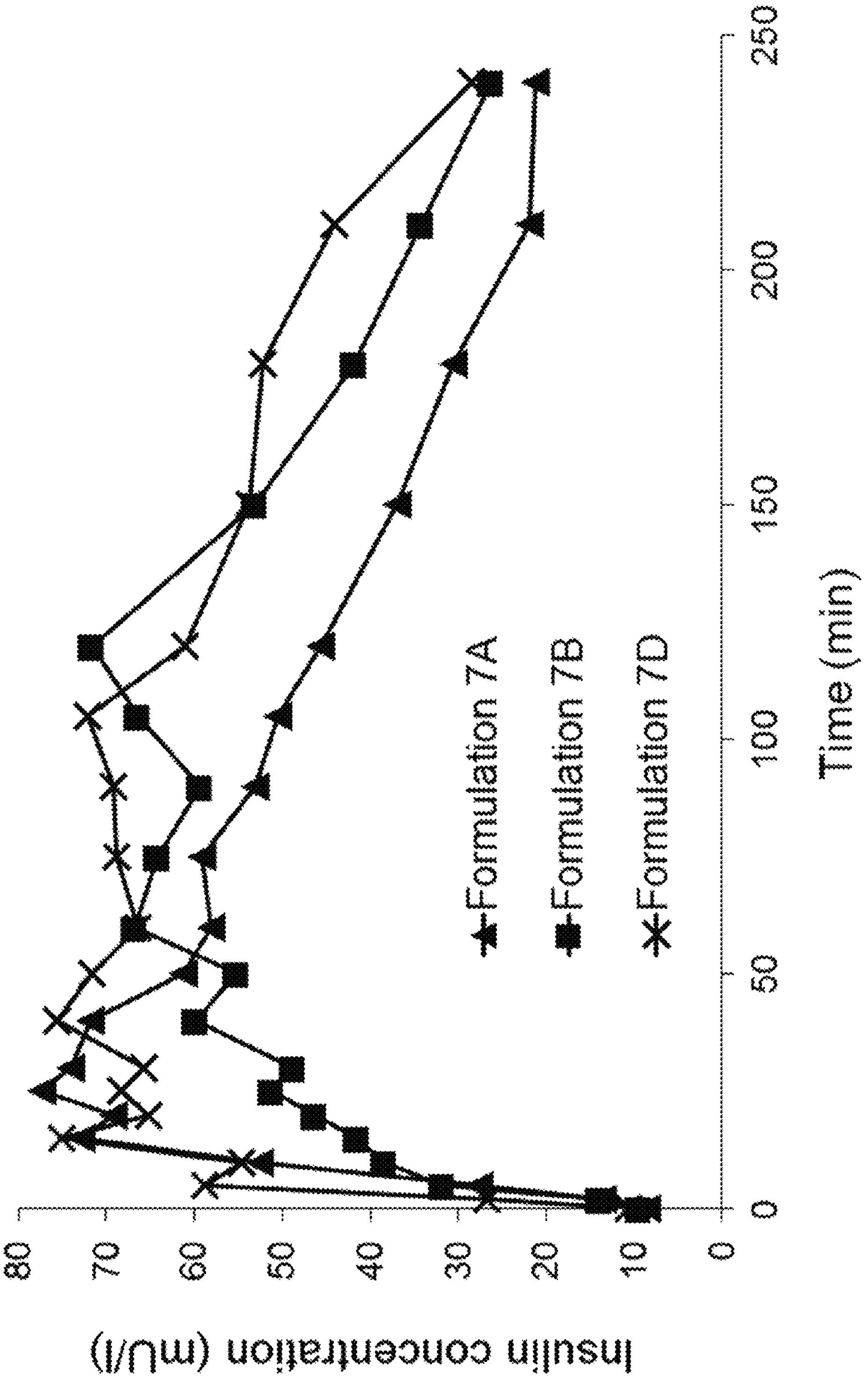

FIG. 2. Pharmacokinetic profiles of compositions 7A, 7B and 7D of Example 7 in a validated diabetic Yucatan miniature pig model.

DETAILED DESCRIPTION OF THE INVENTION

As used herein, "insulin compound" refers to insulin and insulin analogues.

As used herein, "insulin" refers to native human insulin having an A chain and a B chain as set out in SEQ ID NOS: 1 and 2 and containing and connected by disulfide bridges as in the native molecule (Cys A6-Cys A11, Cys B7 to Cys A7 and Cys-B19-Cys A20). Insulin is suitably recombinant insulin.

"Insulin analogue" refers to an analogue of insulin which is an insulin receptor agonist and has a modified amino acid sequence, such as containing 1 or 2 amino acid changes in the sequence of the A or B chain (especially the B chain). Desirably such amino acid modifications are intended to reduce affinity of the molecule for zinc and thus increase speed of action. Thus, desirably an insulin analogue has a speed of action which is the same as or preferably greater than that of insulin. The speed of action of insulin or an insulin analogue may be determined in the Diabetic Pig Pharmacokinetic/Pharmacodynamic Model (see Examples, General Methods (c)). Exemplary insulin analogues include faster acting analogues such as insulin lispro, insulin aspart and insulin glulisine. These forms of insulin have the human insulin A chain but variant B chains—see SEQ ID NOS: 3-5. Further faster acting analogues are described in EP0214826, EP0375437 and EP0678522 the contents of which are herein incorporated by reference in their entirety. Suitably, the insulin compound is not insulin glargine. Suitably, the insulin compound is not insulin degludec. Suitably, the insulin compound is a rapid-acting insulin compound, wherein "rapid-acting" is defined as an insulin compound which has a speed of action which is greater than that of native human insulin, e.g. as measured using the Diabetic Pig Pharmacokinetic/Pharmacodynamic Model (see Examples, General Methods (c)).

In one embodiment, the insulin compound is recombinant human insulin. In another embodiment, it is insulin lispro. In another embodiment, it is insulin aspart. In another embodiment, it is insulin glulisine. In another embodiment, the insulin compound is not recombinant human insulin.

The term "aqueous liquid pharmaceutical composition", as used herein, refers to a composition suitable for therapeutic use in which the aqueous component is or comprises water, preferably distilled water, deionized water, water for injection, sterile water for injection or bacteriostatic water for injection. The aqueous liquid pharmaceutical compositions of the system of the invention are solution compositions in which all components are dissolved in water.

The concentration of insulin compound in the composition is suitably in the range 400-1000 U/ml e.g. 500-1000 U/ml, e.g. 600-1000 U/ml, e.g. 700-1000 U/ml, e.g. 800-1000 U/ml, e.g. 900-1000 U/ml, e.g. 1000 U/ml.

"U/ml" as used herein describes the concentration of insulin compound in terms of a unit per volume, wherein "U" is the international unit of insulin activity (see e.g. European Pharmacopoeia 5.0, Human Insulin, pp 1800-1802).

The compositions of the system of the invention contain ionic zinc i.e. $Zn^{2+}$ ions. The source of the ionic zinc will typically be a water-soluble zinc salt such as $ZnCl_2$, ZnO, $ZnSO_4$, $Zn(NO_3)_2$ or $Zn(acetate)_2$ and most suitably $ZnCl_2$ or ZnO.

The ionic zinc in the composition is typically present at a concentration of more than 0.05% e.g. more than 0.1% e.g. more than 0.2%, more than 0.3% or more than 0.4% by weight of zinc based on the weight of insulin compound in the composition. Thus, the concentration of the ionic zinc in the composition may be more than 0.5% by weight of zinc based on the weight of insulin compound in the composition, for example 0.5-1%, e.g. 0.5-0.75%, e.g. 0.5-0.6% by weight of zinc based on the weight of insulin compound in the composition. For the purpose of the calculation the weight of the counter ion to zinc is excluded.

In a composition e.g. containing 1000 U/ml of insulin compound the concentration of the ionic zinc will typically be more than 0.15 mM e.g. more than 0.3 mM, e.g. more than 0.6 mM, more than 0.9 mM or more than 1.2 mM. Thus, the concentration of the ionic zinc in the composition may be more than 1.5 mM, for example 1.5-6.0 mM, e.g. 2.0-4.5 mM, e.g. 2.5-3.5 mM.

The compositions of the system of the invention may optionally comprise a zinc binding species e.g. at a concentration of 1 mM or more and, for example, selected from species having a log K with respect to zinc ion binding in the range 4.5-12.3 at 25° C. Suitably, the zinc binding species at a concentration of 1 mM or more is selected from species having a log K with respect to zinc ion binding in the range 4.5-10 at 25° C. Metal binding stability constants listed in the National Institute of Standards and Technology reference database 46 (Critically Selected Stability Constants of Metal Complexes) can be used. The database typically lists log K constants determined at 25° C. Therefore, the suitability of a zinc binding species for the present invention can be determined based on its log K metal binding stability constant with respect to zinc binding, as measured at 25° C. and as quoted by the database. The zinc binding species may also be described as an "accelerator" in the compositions according to the invention. Exemplary zinc binding species include polydendate organic anions. Thus, in a preferred embodiment, the zinc binding species is citrate (log K=4.93) which can, for example, be employed as trisodium or citrate acid. Further examples include pyrophosphate (log K=8.71), aspartate (log K=5.87), glutamate (log K=4.62), cysteine (log K=9.11), cystine (log K=6.67) and glutathione (log K=7.98). Other possible zinc binding species include substances that can contribute a lone pair of electrons or electron density for interaction with ionic zinc such as polydendate amines including ethylenediamine (log K=5.69), diethylenetriamine (DETA, log K=8.88) and triethylenetetramine (TETA, log K=11.95); and aromatic or heteroaromatic substances that can contribute a lone pair of electrons especially those comprising an imidazole moiety such as histidine (log K=6.51). Thus, in one embodiment, the zinc binding species having a log K with respect to zinc ion binding in the range 4.5-12.3 is selected from citrate, pyrophosphate, aspartate, glutamate, cysteine, cystine, glutathione, ethylenediamine, histidine, DETA and TETA.

The most suitable concentration of the zinc binding species will depend on the agent and its log K value and will typically be in the range 1-100 mM. The concentration of zinc binding species can be adjusted according to the particular concentration of insulin compound present in the composition, in order to provide the desired accelerating effect.

For example, the zinc binding species having a log K with respect to zinc ion binding in the range 4.5-12.3 may be present at a concentration of 1-60 mM. Suitably the concentration of the zinc binding species in the composition is 5-60 mM e.g. 5-60 mM, e.g. 10-60 mM, e.g. 20-60 mM, e.g. 30-60 mM, e.g. 40-60 mM, e.g. 40-50 mM, more preferably around 44 mM when the zinc binding species is citrate or histidine for insulin compound 1000 U/ml compositions. In one embodiment, the zinc binding species having a log K with respect to zinc ion binding in the range 4.5-12.3 is present at a concentration of 1-50 mM.

Anionic zinc binding species may be employed as the free acid or a salt form, such as a salt form with sodium or calcium ions, especially sodium ions.

A mixture of zinc binding species may be employed, although a single zinc binding species is preferred.

Suitably the molar ratio of ionic zinc to zinc binding species in the composition is 1:3 to 1:175.

The following ranges are particularly of interest especially for citrate or histidine as zinc binding species: e.g. 1:10-1:175, e.g. 1:10 to 1:100, e.g. 1:10-1:50, e.g. 1:10 to 1:30, e.g. 1:10 to 1:20 (especially for insulin compound 1000 U/ml composition).

For example, a composition containing 1000 U/ml of insulin compound may contain around 3 mM of ionic zinc (i.e. around 197 μg/ml of ionic zinc, i.e. around 0.54% by weight of zinc based on the weight of insulin compound in the composition) and around 30-60 mM e.g. 40-60 mM e.g. 40-50 mM zinc binding species (especially citrate).

In one embodiment, the ratio of insulin compound concentration (U/ml) to zinc binding species (mM) in the composition is in the range 100:1 to 2:1 e.g. 50:1 to 2:1, e.g. 40:1 to 2:1.

In one embodiment, the composition of the system of the invention is substantially free of EDTA and any other zinc binding species having a log K with respect to zinc binding of more than 12.3 as determined at 25° C. Thus, in an embodiment, the compositions of the system of the invention are substantially free of EDTA (log K=14.5). Further examples of zinc binding species which have a log K metal binding stability constant with respect to zinc binding of more than 12.3 to be avoided include EGTA (log K=12.6). In general, the composition of the system of the invention will be substantially free of tetradentate ligands or ligands of higher denticity. In an embodiment, the composition of the system of the invention is substantially free of zinc binding species having a log K with respect to zinc ion binding of 10-12.3 at 25° C. "Substantially free" means that the concentration of zinc binding species which have a log K metal binding stability constant with respect to zinc binding as specified (such as EDTA) is less than 0.1 mM, such as less than 0.05 mM, such as less than 0.04 mM or less than 0.01 mM.

Where present, zinc ion binding species which have acid forms (e.g. citric acid) may be introduced into the aqueous compositions of the system of the invention in the form of a salt of the acid, such as a sodium salt (e.g. trisodium citrate). Alternatively, they can be introduced in the form of the acid with subsequent adjustment of pH to the required level. The present inventors have found that in some circumstances introducing the acid form (such as citric acid) into the composition instead of the salt form (e.g. trisodium citrate) may have advantages in terms of providing superior chemical and physical stability. Thus, in an embodiment, the source of the citrate as zinc ion binding species is citric acid. In an embodiment, the composition comprises (i) an insulin compound (e.g. an insulin compound other than insulin glargine) at a concentration of 400 U/mL or more, (ii) ionic zinc, (iii) a zinc binding species selected from diethylenetriamine (DETA) and triethylenetetramine (TETA), and (iv) a non-ionic surfactant. Such a composition may, for example. be substantially free of ethylenediaminetetraacetate (EDTA) and any other zinc binding species having a log K with respect to zinc ion binding of more than 12.3 at 25° C. The zinc binding species may, for example, be present at a concentration of about 0.05 mM or more e.g. 0.05-5 mM, e.g. 0.05-2 mM. The molar ratio of ionic zinc to the zinc binding species in the composition may, for example, be 2:1 to 1:10. The surfactant may, for example, be an alkyl glycoside especially dodecyl maltoside. Alternatively it may be polysorbate 20 (TWEEN® 20) or polyethylene glycol (2) dodecyl ether (BRIJ® L4). The concentration of the insulin compound may for example be 400-1000 U/ml e.g. 500-1000 U/ml, e.g. 600-1000 U/ml, e.g. 700-1000 U/ml, e.g. 800-1000 U/ml, e.g. 900-1000 U/ml, e.g. 1000 U/ml.

In an embodiment, the composition comprises (i) an insulin compound at a concentration of 400 U/mL or more, (ii) ionic zinc, (iii) a zinc binding species at a concentration of 1 mM or more selected from species having a log K with respect to zinc ion binding in the range 4.5-10 at 25° C., (iv) a zinc binding species selected from species having a log K with respect to zinc ion binding of more than 12.3 at 25° C. at a concentration of less than about 0.3 mM, and (v) a non-ionic surfactant. In an embodiment, the zinc binding species having a log K with respect to zinc ion binding of more than 12.3 at 25° C. is present in the composition at a concentration of between about 0.01 mM and about 0.3 mM. In an embodiment, the zinc binding species having a log K with respect to zinc ion binding of more than 12.3 at 25° C. is selected from ethylenediaminetetraacetate (EDTA), ethyleneglycoltetraacetate (EGTA), tetraethylenepentamine, N-(2-hydroxyethyl)ethylenedinitrilotriacetate (HEDTA), 1-methyl-ethylenedinitrilotriacetate (PDTA), 1-ethyl-ethylenedinitrilotriacetate, 1-propyl-thylenedinitrilotriacetate, 1-carboxyethylene-ethylenedinitrilotriacetate, triethylenetetranitrilohexaacetate, tetraethylenepentanitriloheptaacetate (TPHA) and tris(2-aminoethyl)amine (Tren), and especially is EDTA. For example, the molar ratio of ionic zinc to EDTA as zinc binding species having a log K with respect to zinc ion binding of more than 12.3 at 25° C. is 2:1 to 25:1. In an embodiment, the zinc binding species having a log K with respect to zinc ion binding in the range 4.5-10 at 25° C. is selected from citrate, pyrophosphate, aspartate, glutamate, cysteine, cystine, glutathione, ethylenediamine and histidine and especially is citrate. In an embodiment, the zinc binding species having a log K with respect to zinc ion binding in the range 4.5-10 at 25° C. is present at a concentration of 1-50 mM. In an embodiment, the molar ratio of ionic zinc to zinc binding species having a log K with respect to zinc ion binding in the range 4.5-10 at 25° C. is 1:3 to 1:500. The surfactant may, for example, be an alkyl glycoside especially dodecyl maltoside. Alternatively it may be polysorbate 20 (TWEEN® 20) or polyethylene glycol (2) dodecyl ether (BRIJ® L4). The concentration of the insulin compound may for example be 400-1000 U/ml e.g. 500-1000 U/ml, e.g. 600-1000 U/ml, e.g. 700-1000 U/ml, e.g. 800-1000 U/ml, e.g. 900-1000 U/ml, e.g. 1000 U/ml.

The compositions of the system of the invention contain a non-ionic surfactant.

A suitable class of non-ionic surfactants is the alkyl glycosides. In one embodiment, the alkyl glycoside is selected from the group consisting of dodecyl maltoside, dodecyl glucoside, octyl glucoside, octyl maltoside, decyl glucoside, decyl glucopyranoside, decyl maltoside, tridecyl glucoside, tridecyl maltoside, tetradecyl glucoside, tetradecyl maltoside, hexadecyl glucoside, hexadecyl maltoside, sucrose monooctanoate, sucrose monodecanoate, sucrose monododecanoate, sucrose monotridecanoate, sucrose monotetradecanoate and sucrose monohexadecanoate. In one embodiment, the alkyl glycoside is decyl glucopyranoside. In one preferred embodiment, the alkyl glycoside is dodecyl maltoside.

Another suitable class of non-ionic surfactants is the polysorbates (fatty acid esters of ethoxylated sorbitan), such as polysorbate 20 or polysorbate 80. Polysorbate 20 is a mono ester formed from lauric acid and polyoxyethylene (20) sorbitan in which the number 20 indicates the number of oxyethylene groups in the molecule. Polysorbate 80 is a mono ester formed from oleic acid and polyoxyethylene (20) sorbitan in which the number 20 indicates the number of oxyethylene groups in the molecule. Polysorbate 20 is known under a range of brand names including in particular TWEEN® 20, and also ALKEST® TW 20. Polysorbate 80 is known under a range of brand names including in particular TWEEN® 80, and also ALKEST® TW 80. Other suitable polysorbates include polysorbate 40 and polysorbate 60. Thus, in an embodiment, the non-ionic surfactant is a polysorbate surfactant such as polysorbate 20. In an embodiment, the non-ionic surfactant is polysorbate 80. In an embodiment, the non-ionic surfactant is other than polysorbate 80. In one embodiment, the non-ionic surfactant is other than polysorbate 20.

Another suitable class of non-ionic surfactants is block copolymers of polyethylene glycol and polypropylene glycol, also known as poloxamers, especially poloxamer 188, poloxamer 407, poloxamer 171 and poloxamer 185. Poloxamers are also known under brand names PLURONICS® or KOLIPHORS®. For example, poloxamer 188 is marketed as PLURONIC® F-68. Thus, in an embodiment, the non-ionic surfactant is a block copolymer of polyethylene glycol and polypropylene glycol. In an embodiment, the block copolymer of polyethylene glycol and polypropylene glycol is poloxamer 188, poloxamer 407, poloxamer 171 or poloxamer 185.

Another suitable class of non-ionic surfactants is alkyl ethers of polyethylene glycol, especially those known under a brand name BRIJ®, such as selected from polyethylene glycol (2) hexadecyl ether (BRIJ® 52), polyethylene glycol (2) oleyl ether (BRIJ® 93) and polyethylene glycol (2) dodecyl ether (BRIJ® L4). Other suitable BRIJ® surfactants include polyethylene glycol (4) lauryl ether (BRIJ® 30), polyethylene glycol (10) lauryl ether (BRIJ® 35), polyethylene glycol (20) hexadecyl ether (BRIJ® 58) and polyethylene glycol (10) stearyl ether (BRIJ® 78). Thus, in an embodiment, the non-ionic surfactant is an alkyl ether of polyethylene glycol.

Another suitable class of non-ionic surfactants are alkylphenyl ethers of polyethylene glycol, especially 4-(1,1,3,3-tetramethylbutyl)phenyl-polyethylene glycol, also known under a brand name TRITON® X-100. Thus, in an embodiment, the non-ionic surfactant is an alkylphenyl ether of polyethylene glycol. In an embodiment, the alkylphenyl ether of polyethylene glycol is 4-(1,1,3,3-tetramethylbutyl) phenyl-polyethylene glycol.

Particularly suitable are non-ionic surfactants with molecular weight of less than 1000 g/mole, especially less than 600 g/mole, such as 4-(1,1,3,3-tetramethylbutyl)phenyl-polyethylene glycol (TRITON® X-100) (647 g/mole), dodecyl maltoside (511 g/mole), octyl glucoside (292 g/mole), polyethylene glycol (2) dodecyl ether (BRIJ® L4) (362 g/mole), polyethylene glycol (2) oleyl ether (BRIJ® 93) (357 g/mole) and polyethylene glycol (2) hexadecyl ether (BRIJ® 52) (330 g/mole). Thus, in an embodiment, the alkyl ether of polyethylene glycol is selected from polyethylene glycol (2) dodecyl ether, polyethylene glycol (2) oleyl ether and polyethylene glycol (2) hexadecyl ether.

The concentration of the non-ionic surfactant in the composition will typically be in the range 1-1000 μg/ml, e.g. 5-500 μg/ml, e.g. 10-200 μg/ml, such as 10-100 μg/ml or around 50 μg/ml. In one embodiment, the non-ionic surfactant is present at a concentration of 10-400 μg/ml e.g. 20-400 μg/ml, 50-400 μg/ml, 10-300 μg/ml, 20-300 μg/ml, 50-300 μg/ml, 10-200 μg/ml, 20-200 μg/ml, 50-200 μg/ml, 10-100 μg/ml, 20-100 μg/ml or 50-100 μg/ml.

In another embodiment, the concentration of insulin compound is 800-1000 U/ml and the non-ionic surfactant is present at a concentration of 50-200 μg/ml. In this embodiment, suitably the non-ionic surfactant is dodecyl maltoside.

In one embodiment, the composition of the system of the invention comprises (i) an insulin compound at a concentration of 400 U/ml or more (ii) ionic zinc, (iii) optionally citrate as a zinc binding species at a concentration of 1 mM or more, and (iv) a non-ionic surfactant, e.g. an alkyl glycoside; and wherein the composition is substantially free of EDTA and any other zinc binding species having a log K with respect to zinc ion binding of more than 12.3 at 25° C. Suitably, the citrate may be present in the composition at a concentration of 30-60 e.g. 30-50 mM, e.g. 30-40 mM e.g. 35-45 mM e.g. 40-50 mM. In another embodiment, the composition of the system of the invention comprises (i) an insulin compound at a concentration of 400-1000 U/ml e.g. 500-1000 U/ml (ii) ionic zinc, (iii) optionally citrate as a zinc binding species at a concentration of 1 mM or more, and (iv) a non-ionic surfactant; and wherein the composition is substantially free of EDTA and any other zinc binding species having a log K with respect to zinc ion binding of more than 12.3 at 25° C. Suitably, the citrate may be present in the composition at a concentration of 30-60 e.g. 30-50 mM, e.g. 30-40 mM e.g. 35-45 mM e.g. 40-50 mM.

Suitably the pH of the composition of the system of the invention is in the range 5.5-9.0 e.g. in the range 7.0-7.5. In order to minimise injection pain, the pH is preferably close to physiological pH (around pH 7.4). In one embodiment of the composition of the system of the invention, the pH is in the range 7.0-8.0 e.g. 7.5. In another embodiment of the composition of the system of the invention, the pH is in the range 7.6-8.0 e.g. 7.8.

Suitably, the composition of the system of the invention comprises a buffer (e.g. one or more buffers) in order to stabilise the pH of the composition, which can also be selected to enhance protein stability. In one embodiment, a buffer is selected to have a $pK_a$ close to the pH of the composition; for example, histidine is suitably employed as a buffer when the pH of the composition is in the range 5.0-7.0. Such a buffer may be employed in a concentration of 0.5-20 mM e.g. 2-5 mM. If histidine is included in the composition as a zinc binding species it will also have a buffering role at this pH. In another embodiment, the composition comprises a phosphate buffer e.g. sodium phosphate. Sodium phosphate is suitably employed as a buffer when the pH of the composition is in the range 6.1-8.1. Such a buffer may be employed in a concentration of 0.5-20 mM e.g. 2-5 mM e.g. 2 mM. Alternatively, in another embodiment, the composition of the system of the invention is further stabilised as disclosed in WO2008/084237 (herein incorporated by reference in its entirety), which describes a composition comprising a protein and one or more additives, characterised in that the system is substantially free of a conventional buffer, i.e. a compound with an ionisable group having a $pK_a$ within 1 unit of the pH of the composition at the intended temperature range of storage of the composition, such as 25° C. In this embodiment, the pH of the composition is set to a value at which the composition has maximum measurable stability with respect to pH; the one or more additives (displaced buffers) are capable of exchanging protons with the insulin compound and have $pK_a$ values at least 1 unit more or less than the pH of the composition at the intended temperature range of storage of the composition. The additives may have ionisable groups having $pK_a$ between 1 to 5 pH units, preferably between 1 to 3 pH units, most preferably from 1.5 to 2.5 pH units, of the pH of the aqueous composition at the intended temperature range of storage of the composition (e.g. 25° C.). Such additives may typically be employed at a concentration of 0.5-10 mM e.g. 2-5 mM.

The compositions of the system cover a wide range of osmolarity, including hypotonic, isotonic and hypertonic compositions. Preferably, the composition of the system of the invention is substantially isotonic. Suitably the osmolarity of the composition is selected to minimize pain according to the route of administration e.g. upon injection.

Preferred compositions have an osmolarity in the range of about 200 to about 500 mOsm/L. Preferably, the osmolarity is in the range of about 250 to about 350 mOsm/L. More preferably, the osmolarity is about 300 mOsm/L.

Tonicity of the composition may be adjusted with a tonicity modifying agent (e.g. one or more tonicity modifying agents). Thus, the composition of the system of the invention may further comprise a tonicity modifying agent (e.g. one or more tonicity modifying agents). Tonicity modifying agents may be charged or uncharged and uncharged tonicity modifying agents are preferred. Examples of charged tonicity modifying agents include salts such as a combination of sodium, potassium, magnesium or calcium ions, with chloride, sulfate, carbonate, sulfite, nitrate, lactate, succinate, acetate or maleate ions (especially sodium chloride or sodium sulphate, particularly sodium chloride). The insulin compound compositions of the system of the invention may contain a residual NaCl concentration of 2-4 mM as a result of the use of standard acidification and subsequent neutralization steps employed in preparing insulin compositions. Amino acids such as arginine, glycine or histidine may also be used for this purpose. Charged tonicity modifying agent (e.g. NaCl) may be used at a concentration of 100-300 mM, e.g. around 150 mM. In one embodiment, the composition of the system of the invention comprises <10 mM chloride (e.g. sodium chloride), for example <9 mM, <8 mM, <7 mM, <6 mM or <5 mM, or is substantially free of chloride (e.g. sodium chloride) i.e. no chloride is added to the composition beyond any chloride that may be contributed as part of pH adjustment.

Examples of uncharged tonicity modifying agents include sugars, sugar alcohols and other polyols, such as trehalose, sucrose, mannitol, glycerol, 1,2-propanediol, raffinose, lactose, dextrose, sorbitol or lactitol (especially trehalose, mannitol, glycerol or 1,2-propanediol, particularly glycerol). In one embodiment, the uncharged tonicity modifying agent is selected from the group consisting of trehalose, mannitol, glycerol and 1,2-propanediol. In another embodiment, the uncharged tonicity modifying agent is glycerol. Uncharged tonicity modifying agent is preferably used at a concentration of 200-500 mM, e.g. around 300 mM. Another range of interest is 100-500 mM. In one embodiment, the uncharged tonicity modifying agent in the composition is at a concentration of 100-300 mM, e.g. 150-200 mM, 170-180 mM or around 174 mM. In one embodiment, the uncharged tonicity modifying agent in the composition is glycerol at a concentration of 100-300 mM, e.g. 150-200 mM, 170-180 mM or around 174 mM.

When the insulin compound is insulin lispro, the tonicity is suitably adjusted using an uncharged tonicity modifying agent, preferably at a concentration of 200-500 mM, e.g. around 300 mM. In this embodiment, the uncharged tonicity modifying agent is suitably selected from the group consisting of trehalose, mannitol, glycerol and 1,2-propanediol (most suitably glycerol). In another embodiment, the uncharged tonicity modifying agent is used at a concentration of 100-300 mM, e.g. 150-200 mM, 170-180 mM or around 174 mM. In one embodiment, the uncharged tonicity modifying agent is glycerol at a concentration of 100-300 mM, e.g. 150-200 mM, 170-180 mM or around 174 mM.

When the insulin compound is insulin aspart, the tonicity is suitably adjusted using an uncharged tonicity modifying agent, preferably at a concentration of 200-500 mM, e.g. around 300 mM. In this embodiment, the uncharged tonicity modifying agent is suitably selected from the group consisting of trehalose, mannitol, glycerol and 1,2-propanediol (most suitably glycerol). In another embodiment, the uncharged tonicity modifying agent is used at a concentration of 100-300 mM, e.g. 150-200 mM, 170-180 mM or around 174 mM. In one embodiment, the uncharged tonicity modifying agent is glycerol at a concentration of 100-300 mM, e.g. 150-200 mM, 170-180 mM or around 174 mM.

When the insulin compound is insulin glulisine, the tonicity is suitably adjusted using an uncharged tonicity modifying agent, preferably at a concentration of 200-500 mM, e.g. around 300 mM. In this embodiment, the uncharged tonicity modifying agent is suitably selected from the group consisting of trehalose, mannitol, glycerol and 1,2-propanediol (most suitably glycerol). In another embodiment, the uncharged tonicity modifying agent is used at a concentration of 100-300 mM, e.g. 150-200 mM, 170-180 mM or around 174 mM. In one embodiment, the uncharged tonicity modifying agent is glycerol at a concentration of 100-300 mM, e.g. 150-200 mM, 170-180 mM or around 174 mM.

The ionic strength of a composition may be calculated according to the formula I:

$$I = 0.5 \times \sum_{X=1}^{n} c_x z_x^2$$

in which $c_x$ is molar concentration of ion x (mol $L^{-1}$), $z_x$ is the absolute value of the charge of ion x and the sum covers all ions (n) present in the composition. The contribution of the insulin compound itself should be ignored for the purposes of the calculation. The contribution of the zinc binding species (if present) should be ignored for the purposes of the calculation. The contribution of the ionic zinc should be included for the purposes of the calculation. For zwitterions, the absolute value of the charge is the total charge excluding polarity, e.g. for glycine the possible ions have absolute charge of 0, 1 or 2 and for aspartate the possible ions have absolute charge of 0, 1, 2 or 3.

In an embodiment, the ionic strength of the composition is suitably less than 40 mM, less than 30 mM, less than 20 mM or less than 10 mM.

In one embodiment the composition of the system of the invention comprises (i) an insulin compound at a concentration of 400-1000 U/ml e.g. 500-1000 U/ml (ii) ionic zinc, (iii) optionally citrate as a zinc binding species at a concentration of 1 mM or more, and (iv) a non-ionic surfactant e.g. an alkyl glycoside; wherein the composition is substantially free of EDTA and any other zinc binding species having a log K with respect to zinc ion binding of more than 12.3 at 25° C., and wherein the ionic strength of the composition is less than 40 mM, said ionic strength is calculated according to the formula:

$$I = 0.5 \times \sum_{X=1}^{n} c_x z_x^2$$

in which $c_x$ is molar concentration of ion x (mol $L^{-1}$), $z_x$ is the absolute value of the charge of ion x and the sum covers all ions (n) present in the composition, wherein the contribution of the insulin compound and zinc binding species (if present) should be ignored for the purposes of the calculation. The contribution of ionic zinc should be included. Suitably, the citrate is present in the composition at a concentration of 30-50 mM e.g. 40-50 mM.

In one embodiment, the insulin compound is present at a concentration 400-1000 U/ml, >400-1000 U/ml, 500-1000 U/ml, >500-1000 U/ml, 600-1000 U/ml, >600-1000 U/ml, 700-1000 U/ml, >700-1000 U/ml, 750-1000 U/ml, >750-1000 U/ml, 800-1000 U/ml, >800-1000 U/ml, 900-1000 U/ml, >900-1000 U/ml or 1000 U/ml, and the ionic strength taking account of ions in the composition except for the zinc binding species and the insulin compound is less than 40 mM, e.g. less than 30 mM, e.g. less than 20 mM, e.g. less than 10 mM such as 1-10 mM. In a further embodiment, the ionic strength taking account of ions in the composition except for the zinc binding species and the insulin compound is less than 35 mM, less than 30 mM, less than 25 mM, less than 20 mM, less than 15 mM, or less than 10 mM, or is in the range 5-<40 mM, 5-30 mM, 5-20 mM, 2-20 mM, 1-10 mM, 2-10 mM or 5-10 mM.

When the insulin compound is insulin lispro at a concentration of 400-1000 U/ml, >400-1000 U/ml, 500-1000 U/ml, >500-1000 U/ml, 600-1000 U/ml, >600-1000 U/ml, 700-1000 U/ml, >700-1000 U/ml, 750-1000 U/ml, >750-1000 U/ml, 800-1000 U/ml, >800-1000 U/ml, 900-1000 U/ml, >900-1000 U/ml or 1000 U/ml, the ionic strength of the composition is suitably kept to a minimum level since higher ionic strength compositions are less stable than lower ionic strength compositions, particularly at high concentrations of insulin. Suitably the ionic strength taking account of ions in the composition except for the zinc binding species and the insulin compound is less than 40 mM, e.g. less than 30 mM, e.g. less than 20 mM, e.g. less than 10 mM such as 1-10 mM. In particular, the ionic strength taking account of ions in the composition except for the zinc binding species and the insulin compound is less than 35 mM, less than 30 mM, less than 25 mM, less than 20 mM, less than 15 mM, or less than 10 mM, or is in the range 5-<40 mM, 5-30 mM, 5-20 mM, 2-20 mM, 1-10 mM, 2-10 mM or 5-10 mM.

When the insulin compound is insulin aspart at a concentration of 400-1000 U/ml, >400-1000 U/ml, 500-1000 U/mL, >500-1000 U/mL, 600-1000 U/mL, >600-1000 U/mL, 700-1000 U/mL, >700-1000 U/mL, 750-1000 U/mL, >750-1000 U/mL, 800-1000 U/mL, >800-1000 U/mL, 900-1000 U/mL, >900-1000 U/mL or 1000 U/mL, the ionic strength of the composition is suitably kept to a minimum level since higher ionic strength compositions are less stable than lower ionic strength compositions. Suitably the ionic strength taking account of ions in the composition except for the zinc binding species and the insulin compound is less than 40 mM, e.g. less than 30 mM, e.g. less than 20 mM, e.g. less than 10 mM. In this case, tonicity may suitably be adjusted using an uncharged tonicity modifying agent. In particular, the ionic strength taking account of ions in the composition except for the zinc binding species and the insulin compound is less than 35 mM, less than 30 mM, less than 25 mM, less than 20 mM, less than 15 mM, or less than 10 mM, or is in the range 5-<40 mM, 5-30 mM, 5-20 mM, 2-20 mM, 1-10 mM, 2-10 mM or 5-10 mM.

When the insulin compound is insulin glulisine at a concentration of 400-1000 U/ml, >400-1000 U/ml, 500-1000 U/mL, >500-1000 U/mL, 600-1000 U/mL, >600-1000 U/mL, 700-1000 U/mL, >700-1000 U/mL, 750-1000 U/mL, >750-1000 U/mL, 800-1000 U/mL, >800-1000 U/mL, 900-1000 U/mL, >900-1000 U/mL or 1000 U/mL, the ionic strength of the composition is suitably kept to a minimum level since higher ionic strength compositions may be less stable than lower ionic strength compositions. Suitably the ionic strength taking account of ions in the composition except for the zinc binding species and the insulin compound is less than 40 mM, e.g. less than 30 mM, e.g. less than 20 mM, e.g. less than 10 mM. In this case, tonicity may suitably be adjusted using an uncharged tonicity modifying agent. In particular, the ionic strength taking account of ions in the composition except for the zinc binding species and the insulin compound is less than 35 mM, less than 30 mM, less than 25 mM, less than 20 mM, less than 15 mM, or less than 10 mM, or is in the range 5-<40 mM, 5-30 mM, 5-20 mM, 2-20 mM, 1-10 mM, 2-10 mM or 5-10 mM.

The composition of the system of the invention may optionally further comprise a preservative (e.g. one or more preservatives). One or more preservatives may be employed. In one embodiment, the preservative is selected from the group consisting of phenol, m-cresol, chlorocresol, benzyl alcohol, propylparaben, methylparaben, benzalkonium chloride and benzethonium chloride.

The composition of the system of the invention may optionally further comprise nicotinamide. The presence of nicotinamide may further increase the speed of onset of action of insulin formulated in compositions of the system of the invention. Suitably, the concentration of nicotinamide is in the range 10-150 mM, preferably in the range 20-100 mM, such as around 80 mM.

The composition of the system of the invention may optionally further comprise nicotinic acid or a salt thereof. The presence of nicotinic acid or a salt thereof may also further increase the speed of onset of action of insulin formulated in compositions of the system of the invention. Suitably, the concentration of nicotinic acid or a salt thereof is in the range 10-150 mM, preferably in the range 20-100 mM, such as around 80 mM. Example salts include metal salts such as sodium, potassium and magnesium salts.

Typically, one of nicotinamide and nicotinic acid (or as salt thereof) may be included in the composition but not both.

In an embodiment, the composition comprises (i) an insulin compound at a concentration of 400 U/mL or more, (ii) ionic zinc, (iii) a nicotinic compound, (iv) a non-ionic surfactant; and (v) a salt selected from the salts formed between Group 1 metals and a mono or divalent anion. In an embodiment, the nicotinic compound is nicotinamide or nicotinic acid or a salt thereof. In an embodiment, the nicotinic compound is present in the composition at a concentration of 10-150 mM. In an embodiment, the Group 1 metal is sodium. In an embodiment, the salt is the sodium salt of a mono or divalent anion. In an embodiment, the anion is chloride or acetate. Thus, for example, the salt is sodium chloride or sodium acetate. In an embodiment, the salt is present in the composition at a concentration of 30-200 mM. The surfactant may, for example, be an alkyl glycoside especially dodecyl maltoside. Alternatively it may be polysorbate 20 (TWEEN® 20) or polyethylene glycol (2) dodecyl ether (BRIJ® L4). The concentration of the insulin compound may for example be 400-1000 U/ml e.g. 500-1000 U/ml, e.g. 600-1000 U/ml, e.g. 700-1000 U/ml, e.g. 800-1000 U/ml, e.g. 900-1000 U/ml, e.g. 1000 U/ml.

The composition of the system of the invention may optionally further comprise treprostinil or a salt thereof. The presence of the treprostinil may further increase the speed of onset of action of insulin formulated in compositions of the system of the invention. Suitably, the concentration of treprostinil in the composition is in the range of 0.1-12 μg/ml e.g. 0.1-10 μg/ml, 0.1-9 μg/ml, 0.1-8 μg/ml, 0.1-7 μg/ml, 0.1-6 μg/ml, 0.1-5 μg/ml, 0.1-4 μg/ml, 0.1-3 μg/ml, 0.1-2 μg/ml, 0.5-2 μg/ml e.g. about 1 μg/ml.

In one embodiment, the composition does not contain a vasodilator. In a further embodiment, the composition does not contain treprostinil, nicotinamide, nicotinic acid or a salt thereof.

Compositions of the system of the invention may optionally include other beneficial components including stabilising agents. For example, amino acids such as arginine or proline may be included which may have stabilising properties. Thus, in one embodiment, the compositions of the system of the invention comprise arginine.

In an embodiment of the invention the compositions are free of acids selected from glutamic acid, ascorbic acid, succinic acid, aspartic acid, maleic acid, fumaric acid, adipic acid and acetic acid and are also free from the corresponding ionic forms of these acids.

In an embodiment of the invention the compositions of the system are free of arginine.

In an embodiment of the invention the compositions of the system are free of protamine and protamine salts.

In an embodiment of the invention the compositions of the system are free of magnesium ions.

The addition of magnesium ions e.g. in the form of magnesium chloride may provide a stabilising effect. Thus, in an embodiment of the invention the composition of the system contains magnesium ions e.g. $MgCl_2$.

In an embodiment of the invention the compositions of the system are free of calcium ions.

Compositions of the system may further comprise an additional therapeutically active agent (an "active agent"), in particular an agent of use in the treatment of diabetes (i.e. in addition to the insulin compound in particular the rapid-acting insulin compound) e.g. an amylin analogue or a GLP-1 agonist. In one embodiment, the composition further comprises an amylin analogue such as pramlintide, suitably ata concentration of 0.1-10 mg/ml e.g. 0.2-6 mg/ml. In one embodiment, the composition further comprises a GLP-1 agonist such as liraglutide, dulaglutide, albiglutide, exenatide or lixisenatide, suitably at a concentration of 10 μg/ml to 50 mg/ml e.g. 200 μg/ml to 10 mg/ml or 1 mg/ml to 10 mg/ml.

Suitably the compositions of the system are sufficiently stable that the concentration of high molecular weight species remains low upon extended storage. The term "high molecular weight species" as used herein, refers to any irreversibly formed component of the protein content which has an apparent molecular weight at least about double the molecular weight of the parent insulin compound, as detected by a suitable analytical method, such as size-exclusion chromatography. That is, high molecular weight species are multimeric aggregates of the parent insulin compound. The multimeric aggregates may comprise the parent protein molecules with considerably altered conformation or they may be an assembly of the parent protein units in the native or near-native conformation. The determination of high molecular weight species can be done using methods known in the art, including size exclusion chromatography, electrophoresis, analytical ultracentrifugation, light scattering, dynamic light scattering, static light scattering and field flow fractionation.

Suitably the compositions of the system are sufficiently stable that they remain substantially free of visible particles after storage at 30° C. for at least one month or more, two months or more, or three months or more. Visible particles are suitably detected using the 2.9.20. European Pharmacopoeia Monograph (Particulate Contamination: Visible Particles). For example, a composition is substantially free of visible particles if it has a Visual score according to Visual Assessment Scoring Method A of 1, 2 or 3, especially 1 or 2 according to the definition given in the Examples section.

Suitably the compositions of the system are sufficiently stable that there is minimal increase in soluble aggregates such as <0.5%, <0.2% or <0.1% increase after storage at 30° C. for one month or more, two months or more or three months or more. Soluble aggregates are suitable detected using SEC (see General Methods).

Suitably the compositions of the system are sufficiently stable that the concentration of related species remains low upon extended storage. The term "related species" as used herein, refers to any component of the protein content formed by a chemical modification of the parent insulin compound, particularly desamido or cyclic imide forms of insulin. Related species are suitably detected by RP-HPLC.

In a preferred embodiment, the composition of the system of the invention retains at least 95%, e.g. at least 96%, e.g. at least 97%, e.g. at least 98%, e.g. at least 99% parent insulin compound (by weight of total protein) after storage at 30° C. for one, two or three months. The percentage of insulin compound (by weight of total protein) may be determined by size-exclusion chromatography or RP-HPLC.

In a preferred embodiment, the composition of the system of the invention comprises no more than 4% (by weight of total protein), preferably no more than 2% high molecular weight species (e.g. visible particles and/or soluble aggregates) after storage at 30° C. for one, two or three months.

In a preferred embodiment, the composition of the system of the invention comprises no more than 4% (by weight of total protein), preferably no more than 2%, preferably no more than 1% A-21 desamido form of the insulin compound after storage at 30° C. for one, two or three months.

In preferred embodiments, a composition of the system of the invention should exhibit an increase in high molecular weight species (e.g. visible particles and/or soluble aggregates) during storage which is at least 10% lower, preferably at least 25% lower, more preferably at least 50% lower, than a composition lacking the non-ionic surfactant but otherwise identical, following storage under the same conditions (e.g. 30° C.) and length of time (e.g. one, two or three months).

In preferred embodiments, a composition of the system of the invention should exhibit an increase in related species during storage which is at least 10% lower, preferably at least 25% lower, more preferably at least 50% lower, than a composition lacking the non-ionic surfactant but otherwise identical, following storage under the same conditions (e.g. 30° C.) and length of time (e.g. one, two or three months).

The speed of action of a composition of the system of the invention may be determined in the Diabetic Pig Pharmacokinetic/Pharmacodynamic Model (see Examples, General Methods (c)). In preferred embodiments, a composition of the present invention exhibits a $T_{max}$ (i.e. time to peak insulin concentration) that is at least 20% shorter, preferably at least 30% shorter than a composition lacking the zinc binding species having a log K with respect to zinc ion binding in the range 4.5-12.3 (e.g. in the range 4.5-10) at 25° C. but otherwise identical, using the model. In preferred embodiments, a composition of the present invention exhibits an area under the curve on the pharmacodynamics profile within the first 45 minutes after injection that is at least 20% greater, preferably at least 30% greater than a composition lacking the zinc binding species having a log K with respect to zinc ion binding in the range 4.5-12.3 (e.g. in the range 4.5-10) at 25° C. but otherwise identical, using the model.

In one embodiment, the composition of the system of the invention comprises (i) insulin lispro at a concentration of 400-1000 U/ml e.g. 500-1000 U/ml, (ii) ionic zinc, (iii)

optionally a zinc binding species at a concentration of 1 mM or more selected from species having a log K with respect to zinc ion binding in the range 4.5-12.3 at 25° C. e.g. citrate, and (iv) a non-ionic surfactant e.g. an alkyl glycoside; and wherein the composition is substantially free of EDTA and any other zinc binding species having a log K with respect to zinc ion binding of more than 12.3 at 25° C., which exhibits a $T_{max}$ (i.e. time to peak insulin concentration) that is at least 20% shorter, preferably at least 30% shorter than an aqueous composition consisting of: insulin lispro (100 U/ml), sodium phosphate (13.2 mM), glycerol (174 mM), m-cresol (29 mM), ionic zinc (19.7 μg/ml, excluding counter-ion) adjusted to pH 7.3, using the Diabetic Pig Pharmacokinetic/Pharmacodynamic Model (see Examples, General Methods (c)). In another embodiment, the present invention provides a composition comprising (i) insulin lispro at a concentration of 400-1000 U/ml e.g. 500-1000 U/ml, (ii) ionic zinc, (iii) optionally a zinc binding species at a concentration of 1 mM or more selected from species having a log K with respect to zinc ion binding in the range 4.5-12.3 at 25° C. e.g. citrate, and (iv) a non-ionic surfactant e.g. an alkyl glycoside; and wherein the composition is substantially free of EDTA and any other zinc binding species having a log K with respect to zinc ion binding of more than 12.3 at 25° C., which exhibits an area under the curve on the pharmacodynamics profile within the first 45 minutes after injection that is at least 20% greater, preferably at least 30% greater than an aqueous composition consisting of: insulin lispro (100 U/ml), sodium phosphate (13.2 mM), glycerol (174 mM), m-cresol (29 mM), ionic zinc (19.7 μg/ml, excluding counter-ion) adjusted to pH 7.3, using the Diabetic Pig Pharmacokinetic/Pharmacodynamic Model (see Examples, General Methods (c)).

In one embodiment, the composition of the system of the invention comprises (i) insulin aspart at a concentration of 400-1000 U/ml e.g. 500-1000 U/ml, (ii) ionic zinc, (iii) optionally a zinc binding species at a concentration of 1 mM or more selected from species having a log K with respect to zinc ion binding in the range 4.5-12.3 at 25° C. e.g. citrate, and (iv) a non-ionic surfactant e.g. an alkyl glycoside; and wherein the composition is substantially free of EDTA and any other zinc binding species having a log K with respect to zinc ion binding of more than 12.3 at 25° C., which exhibits a $T_{max}$ (i.e. time to peak insulin concentration) that is at least 20% shorter, preferably at least 30% shorter than an aqueous composition consisting of: insulin aspart (100 U/ml), sodium phosphate (7 mM), glycerol (174 mM), sodium chloride (10 mM), phenol (15.9 mM), m-cresol (15.9 mM) and ionic zinc (19.7 μg/ml, excluding counter-anion) adjusted to pH 7.4, using the Diabetic Pig Pharmacokinetic/Pharmacodynamic Model (see Examples, General Methods (c)). In another embodiment, the present invention provides a composition comprising (i) insulin aspart at a concentration of 400-1000 e.g. 500-1000 U/ml, (ii) ionic zinc, (iii) optionally a zinc binding species at a concentration of 1 mM or more selected from species having a log K with respect to zinc ion binding in the range 4.5-12.3 at 25° C. e.g. citrate, and (iv) a non-ionic surfactant e.g. an alkyl glycoside; and wherein the composition is substantially free of EDTA and any other zinc binding species having a log K with respect to zinc ion binding of more than 12.3 at 25° C., which exhibits an area under the curve on the pharmacodynamics profile within the first 45 minutes after injection that is at least 20% greater, preferably at least 30% greater than an aqueous composition consisting of: insulin aspart (100 U/ml), sodium phosphate (7 mM), glycerol (174 mM), sodium chloride (10 mM), phenol (15.9 mM), m-cresol (15.9 mM) and ionic zinc (19.7 μg/ml, excluding counter-anion) adjusted to pH 7.4, using the Diabetic Pig Pharmacokinetic/Pharmacodynamic Model (see Examples, General Methods (c)).

In preferred embodiments, a composition of the system of the invention is bioequivalent to a standard composition comprising the insulin compound at 100 U/ml.

As used herein, "bioequivalent" means that the composition of the system of the invention has an equivalent or similar pharmacokinetic/pharmacodynamic (PK/PD) profile to a standard composition. For example, the composition of the system of the invention exhibits a $T_{MAX}$ or $T_{1/2\ MAX}$ (measured in accordance with the Diabetic Pig Pharmacokinetic/Pharmacodynamic Model described in section (c) of General Methods) which is substantially the same as (e.g. within ±20% of, e.g. within ±10% of) that of the standard composition. Bioequivalence can also be established by applying the Student's t-test to the pharmacokinetic/pharmacodynamics results achieved using two different compositions as described in the diabetic pig pharmacokinetic/pharmacodynamic model described in section (c) of General Methods.

By "standard composition" is meant a commercially available composition of the same insulin compound at a concentration of 100 U/ml such as HUMALOG® (for insulin lispro) or NOVORAPID® (for insulin aspart) or APIDRA® (for insulin glulisine).

In one embodiment, the composition of the system of the invention comprises an insulin compound at a concentration of 400-1000 U/mL e.g. 500-1000 U/mL and wherein the composition is bioequivalent to a standard composition comprising the insulin compound at a concentration of 100 U/mL. In another embodiment, the absorption of insulin compound into the blood stream of the mammal after administration using the system is bioequivalent to a standard composition at a concentration comprising the insulin compound at a concentration of 100 U/mL. In another embodiment, the glucose reduction response caused by administration of a given amount of insulin compound to the mammal using the system is bioequivalent to a standard composition comprising the insulin compound at a concentration of 100 U/mL.

In one embodiment, a composition of the system of the invention wherein the insulin compound is insulin lispro is bioequivalent to a commercial composition of insulin lispro at a concentration of 100 U/ml e.g. an aqueous composition consisting of: insulin lispro (100 U/ml), sodium phosphate (13.2 mM), glycerol (174 mM), m-cresol (29 mM), ionic zinc (19.7 μg/ml, excluding counter-ion) adjusted to pH 7.3 (i.e. the composition of HUMALOG®).

In one embodiment, a composition of the system of the invention wherein the insulin compound is insulin aspart is bioequivalent to a commercial composition of insulin aspart at a concentration of 100 U/ml e.g. an aqueous composition consisting of: insulin aspart (100 U/ml), sodium phosphate (7 mM), glycerol (174 mM), sodium chloride (10 mM), phenol (15.9 mM), m-cresol (15.9 mM) and ionic zinc (19.7 μg/ml, excluding counter-anion) adjusted to pH 7.4 (i.e. the composition of NOVORAPID®).

According to further aspects of the system of the invention, there is provided a composition of the system of the invention for use in the treatment of a subject suffering from diabetes mellitus. There is also provided a method of treatment of diabetes mellitus which comprises administering to a subject in need thereof an effective amount of a composition of the system of the invention.

In one embodiment, the composition of the system of the invention is co-administered with a long acting insulin such as insulin glargine or insulin degludec, suitably at a concentration of 50-1000 U/ml e.g. 100-500 U/ml or 100-200 U/ml.

The composition of the system of the invention is for administration by infusion, preferably by subcutaneous infusion.

Pumps of the system of the invention may, for example, be syringe pumps wherein the insulin reservoir is in the form of a small syringe and the insulin composition is dispensed by the action of a moveable piston. Various mechanisms can be used to exert the appropriate force onto the piston to deliver the require dose accurately, including (but not limited to) electromechanical effect, piezoelectric effect or electrochemical effect (expansion via electrochemical formation of a gas). Alternatively, the system of the invention may rely on a different pumping mechanism that does not require a syringe and a piston, such as the wax actuated technology (Cellnovo, WO2015114374) or the MICRO-DELIVERY® technology from Tandem ensuring accurate delivery of dose.

The system of the invention can deliver the insulin composition to the mammal at a set basal rate. In one embodiment, the pump delivers the insulin compound in the composition to the mammal at a set basal rate e.g. 0.1-20 U/hr e.g. 1-20 U/hr, e.g. 1-10 U/hr, e.g. 0.1-10 U/hr. The system of the invention may optionally comprise a controller for controlling the basal rate.

The pump of the system delivers the composition in pulses wherein the volume of the pulse is 0.5 μL or less. In one embodiment, the volume of the pulse is 0.2 μL or less. In one embodiment, the volume of the pulse is 0.05 μL or less e.g. 0.001-0.5 μL, e.g. 0.005-0.5 μL, e.g. 0.005-0.05 μL.

In an embodiment, each pulse delivers 0.001-1 U e.g. 0.001-0.1 U of insulin compound. Such pulses of the pump may deliver 0.05-50 ng, e.g. 0.5 ng, e.g. 1 ng, e.g. 5 ng, e.g. 10 ng, e.g. 20 ng, e.g. 50 ng of non-ionic surfactant. Preferably, the ratio between the dose of insulin compound delivered (U) and the pulse volume (μL) is at least 0.4:1 e.g. at least 0.5:1, e.g. at least 0.6:1. In an embodiment, the pump will deliver 10-1000 pulses per hour e.g. 10-500, e.g. 10-250, e.g. 10-200, e.g. 10-150, e.g. 10-100, e.g. 10-75, e.g. 10-50 pulses per hour. In a particular embodiment, the pump will deliver 10-100 pulses per hour. In one embodiment, the pump will deliver 20-1000 pulses per hour e.g. 20-500, e.g. 20-250, e.g. 20-200, e.g. 20-150, e.g. 20-100, e.g. 20-75, e.g. 20-50 pulses per hour. In a particular embodiment, the pump will deliver 20-100 pulses per hour. In an embodiment, the pump will deliver 30-1000 pulses per hour e.g. 30-500, e.g. 30-100, e.g. 30-75, e.g. 30-50 pulses per hour. In a particular embodiment, the pump will deliver 30-100 pulses per hour. In an embodiment, the pump will deliver 40-1000 pulses per hour e.g. 40-250, e.g. 100-500, e.g. 100-1000, e.g. 500-1000 pulses per hour. In a particular embodiment, the pump will deliver 40-100 pulses per hour. The system of the invention may optionally comprise a controller for controlling the size and frequency of the pulses.

The pump of the system may deliver the insulin compound in the composition to the mammal in a bolus dose. Administration of a bolus dose should suitably occur in the window between 15 minutes before eating (i.e. before start of a meal) and 15 minutes after eating (i.e. after end of a meal). In one embodiment, the bolus dose is 1-100 U e.g. 1-10 U, e.g. 2-20 U, e.g. 5-50 U, e.g. 10-100 U, e.g. 50-100 U.

The reservoir of the system which comprises the aqueous liquid pharmaceutical composition for delivery by means of said pump will typically have a total volume of up to 3 mL e.g. 3 mL, e.g. 2 mL, e.g. 1 mL. The system may comprise one or more further reservoirs. In one embodiment, the further reservoirs comprise an aqueous liquid pharmaceutical composition comprising an insulin compound as active ingredient. In another embodiment, the further reservoirs comprise an aqueous composition comprising an active ingredient which is not an insulin compound.

Reservoirs of the system are retained in containers e.g. cartridges or syringes. Containers may be a replaceable or refillable component of the system. The system may optionally further comprise a glucose sensor and control means to direct the pump to deliver a dose of insulin compound based on information received from the glucose sensor. The glucose sensor provides glucose readings at regular intervals, e.g. every 5 minutes. This is referred to as the Continuous Glucose Monitoring (CGM).

The system of the invention may be either be an open-loop system or a closed-loop system.

In an open-loop system the infusion pump supplies a predetermined amount of Insulin and the wearer is expected to manually adjust the dosing based on the CGM readings to ensure the glucose level remains within the required range.

In a closed-loop system, a disposable sensor measures interstitial glucose levels, which are fed through wireless transmission into the insulin pump controlled by an algorithm controlling delivery of insulin into the subcutaneous tissue. In such system, involvement of wearer to maintain the blood glucose control is minimal. Such a closed loop system is sometimes referred to as an artificial pancreas. The success of the closed-loop system algorithms depends considerably on the speed of onset of the insulin compound used in the pump. The more rapid the onset is the more accurately can the algorithm correct the insulin level to ensure the blood glucose remains within the normal range as much as possible.

Another aspect of the invention is a medical infusion pump system comprising a reservoir comprising a plurality of doses of the composition and a pump adapted for automatic or remote operation such that upon automatic or remote operation one or more doses of the composition is administered to the body e.g. subcutaneously or intramuscularly. Such devices may be worn on the outside of the body or implanted in the body.

In one embodiment, the system may be worn on the surface of the body. Suitably, the system is worn on the surface of the body for 1 day or more, e.g. 2 days or more, e.g. 3 days or more, e.g. 5 days or more, e.g. 7 days or more.

The system may comprise at least one cannula or needle in fluid communication with the pump or the at least one reservoir for subcutaneously infusing the insulin composition into the mammal.

In one embodiment, the cannula or the needle is attached to the main body of the pump via a tubing.

In one embodiment, the cannula or the needle is an inherent part of the pump. The cannula is inserted automatically after attaching the pump on the skin, typically by programming the activation of the pump from a remote device. In one embodiment, the system is a patch pump system.

In another embodiment, the system is implanted in the body.

Medical infusion pump systems provide a demanding environment for preserving the activity of insulin. For example, the reservoirs of such systems are exposed to warmth (37° C. if implanted or slightly lower if worn on the body), agitation (due to movement of the body) and shear stresses (due to operation of the pump).

In an embodiment, a composition of the system of the invention is more stable than in the absence of non-ionic surfactant in-use i.e. during operation of the pump for 3 days or more, e.g. 3 days, e.g. 5 days or more, e.g. 5 days, e.g. 7 days or more, e.g. 7 days, e.g. 10 days or more, e.g. 10 days, e.g. 14 days or more, e.g. 14 days, e.g. 21 days or more, e.g. 21 days, e.g. 28 days. For example, a composition of the system of the invention forms fewer visible particles and/or soluble aggregates than an identical composition in the absence of alkyl glucoside in-use i.e. during operation of the pump for 3 days or more, e.g. 3 days, e.g. 5 days or more, e.g. 5 days, e.g. 7 days or more, e.g. 7 days, e.g. 10 days or more, e.g. 10 days, e.g. 14 days or more, e.g. 14 days, e.g. 21 days or more, e.g. 21 days, e.g. 28 days.

In an embodiment, said stability in-use is indicated by the presence of fewer visible particles and/or soluble aggregates in the reservoir after the said number of days. In an embodiment, said stability is indicated by the presence of fewer visible particles and/or soluble aggregates in a pulsed dose after the said number of days.

Visible particles and soluble aggregates can be determined by Visual Assessment Scoring Method A and SEC (see General Methods).

The system may optionally further comprise a glucose sensor and control means to direct the pump to deliver a dose of insulin compound based on information received from the glucose sensor.

In an embodiment, the system administers the composition subcutaneously to the mammal. In an aspect of the invention, there is provided use of the system in the treatment of diabetes mellitus in said mammal. In an embodiment, the mammal is a human.

In another embodiment, there is provided method of treatment of diabetes mellitus which comprises administering to a mammal in need thereof an effective amount of an insulin compound containing composition via a pump using the system of the invention. Suitably, the mammal is a human.

Compositions of the system of the invention may be prepared by mixing the ingredients. For example, the insulin compound may be dissolved in an aqueous composition comprising the other components. Alternatively, the insulin compound may be dissolved in a strong acid (typically HCl), after dissolution diluted with an aqueous composition comprising the other components, and then pH adjusted to the desired pH with addition of alkali (e.g. NaOH). As a variation on this method, a step of neutralising the acid solution may be performed before the dilution step and it may then not be necessary to adjust the pH after the dilution step (or a small adjustment only may be necessary).

In another aspect of the invention, there is provided the use of a non-ionic surfactant, e.g. an alkyl glycoside, to improve the stability of an insulin compound in an aqueous liquid pharmaceutical composition in a medical infusion pump system comprising a pump and an aqueous composition for delivery by means of said pump to a mammal, wherein the composition comprises (i) an insulin compound, (ii) ionic zinc and (iii) a non-ionic surfactant.

In a further aspect of the invention, there is provided a method of improving the stability of an insulin compound to be administered by a medical infusion pump, which comprises adding a non-ionic surfactant to an aqueous liquid pharmaceutical composition comprising the insulin compound and ionic zinc.

Systems of the invention in at least some embodiments are expected to have one or more of the following advantageous properties:

- The systems can deliver high strength insulin that is rapid acting or ultra-rapid acting;
- The systems improve the convenience for the user by being suitably small whilst delivering insulin that is rapid acting or ultra-rapid acting;
- The systems can be used for extended periods of time, such as 3 days or more, thus improving user convenience;
- The systems can minimise the incidence of an occlusion by reducing the formation of visible particles and/or soluble aggregates derived from the insulin compound;
- Compositions of the system have good physical stability during use, for example after use for a number of days as an implanted system or a system worn on the body;
- Compositions of the system have good physical stability upon storage, especially as measured by the amount of HMWS e.g. visible particles and/or soluble aggregates;
- Compositions of the system have good chemical stability upon storage, especially as measured by the amount of related products e.g. products of deamidation;
- Compositions of the system have rapid speed of action, typically faster than normal human insulin, upon administration to a subject;
- Compositions of the system have rapid speed of action, typically as fast as a standard composition with insulin compound concentration of 100 U/ml;
- Compositions of the system have high insulin concentration while maintaining a rapid speed of action.

Abbreviations

DETA diethylenetriamine
EDTA ethylenediaminetetraacetate
EGTA ethyleneglycoltetraacetate
HPLC high performance liquid chromatography
HMWS high molecular weight species
RP reverse phase
SEC size-exclusion chromatography
TETA triethylenetetramine
PD pharmacodynamic
PK pharmacokinetic

EXAMPLES

General Methods (a) Size Exclusion Chromatography (SEC)

Ultra-high performance size exclusion chromatography of insulin preparations was performed using the Waters ACQUITY H-class Bio UPLC® system with a 1.7 μm Ethylene Bridged Hybrid 125 A pore packing material in a 300 mm by 4.6 mm column. The column was equilibrated in 0.65 mg/ml L-arginine, 20% v/v acetonitrile, 15% v/v glacial acetic acid mobile phase and 10 μl of sample, acidified with 0.01M HCl, was analysed at 0.4 mL/min, with 276 nm UV detection. All analyses were performed at ambient temperature.

(b) Reversed-Phase Chromatography (RP-HPLC)

Ultra-high performance reverse phase chromatography was performed using the Waters ACQUITY H-class Bio UPLC® system with a 1.7 μm Ethylene Bridged Hybrid particle, 130 Å pore resin trifunctionally immobilised with a C18 ligand in a 50 mm by 2.1 mm column. Insulin samples were bound in a 82% w/v $Na_2SO_4$, 18% v/v acetonitrile, pH 2.3 mobile phase and eluted in 50% w/v $Na_2SO_4$, 50% v/v acetonitrile gradient flow. 2 μl of sample was acidified with 0.01M HCl and analysed at 0.61 mL/min, with 214 nm UV detection. All analyses were performed at 40° C.

(c) the Diabetic Pig Pharmacokinetic/Pharmacodynamic Model: Method for Determining Speed of Action 10 male diabetic Yucatan miniature pigs were used. Pigs were injected subcutaneously with a sample of the test composition and blood was taken (1 or 2 ml) at various time-points (min) with respect to the injection up to around 240 min after the injection. For pharmacodynamics profile, serum was analysed for glucose (using a commercially available glucometer). For pharmacokinetic profile, insulin concentration was determined in the serum using an immunoassay.

In order to evaluate the compositions for bioequivalence, mean values of $T_{MAX}$ (i.e. time to reach the maximum insulin concentration in serum) and corresponding standard deviation were calculated across the whole set of 10 pigs used in the study. Similarly, mean values of $T_{1/2\ MAX}$ (i.e. time to reach half of the maximum concentration) and corresponding standard deviation were calculated across the whole set of 10 pigs used in the study. Student t-test (95% confidence interval) was subsequently applied to allow assessment of bioequivalence between any two compositions tested. If the p-value of the t-test applied to the results populations of two samples was 0.05 the samples were considered bioequivalent, if the result was <0.05 then the samples were considered non-bioequivalent.

(d) Visual Assessment

Visible particles are suitably detected using the 2.9.20. European Pharmacopoeia Monograph (Particulate Contamination: Visible Particles). The apparatus required consists of a viewing station comprising:

- a matt black panel of appropriate size held in a vertical position
- a non-glare white panel of appropriate size held in a vertical position next to the black panel
- an adjustable lampholder fitted with a suitable, shaded, white-light source and with a suitable light diffuser (a viewing illuminator containing two 13 W fluorescent tubes, each 525 mm in length, is suitable). The intensity of illumination at the viewing point is maintained between 2000 lux and 3750 lux.

Any adherent labels are removed from the container and the outside washed and dried. The container is gently swirled or inverted, ensuring that air bubbles are not introduced, and observed for about 5 s in front of the white panel. The procedure is repeated in front of the black panel. The presence of any particles is recorded.

The visual scores are ranked as follows:

Visual Assessment Scoring Method A

- Visual score 1: Clear solution, virtually free of particles
- Visual score 2: ~5 very small particles
- Visual score 3: ~10-20 very small particles
- Visual score 4: 20-50 particles, including larger particles
- Visual score 5: >50 particles, including larger particles Whilst the particles in samples with visual scores 4 and 5 are clearly detectable on casual visual assessment under normal light, samples with visual score 1-3 generally appear as clear solutions on the same assessment. Samples with visual scores 1-3 are considered to be "Pass"; samples with visual score 4-5 are considered to be "Fail".

Example 1—Example Compositions

The following example compositions may be prepared:

Example A

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 197 μg/ml (3 mM), equals 0.55% (w/w) based on the weight of insulin compound in the composition |
| Citric acid | 44 mM |
| Glycerol | 174 mM |
| Surfactant | Selected from A1, A2 or A3 (see below) |
| Water for injection | qs |
| Residual NaCl | Acidification and subsequent neutralisation during preparation results in formation of 2-4 mM NaCl |
| pH adjusted to 7.4 | |
| Example A1: | surfactant = dodecyl maltoside (0.05 mg/ml) |
| Example A2: | surfactant = polysorbate 20 (TWEEN ® 20) (0.05 mg/ml) |
| Example A3: | surfactant = polyethylene glycol (2) dodecyl ether (BRIJ ® L4) (0.05 mg/ml) |

Example B

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 197 μg/ml (3 mM), equals 0.55% (w/w) based on the weight of insulin compound in the composition |
| Citric acid | 44 mM |
| Glycerol | 174 mM |
| Surfactant | Selected from B1, B2 or B3 (see below) |
| Water for injection | qs |
| Residual NaCl | Acidification and subsequent neutralisation during preparation results in formation of 2-4 mM NaCl |
| pH adjusted to 7.8 | |
| Example B1: | surfactant = dodecyl maltoside (0.05 mg/ml) |
| Example B2: | surfactant = polysorbate 20 (TWEEN ® 20) (0.05 mg/ml) |
| Example B3: | surfactant = polyethylene glycol (2) dodecyl ether (BRIJ ® L4) (0.05 mg/ml) |

Example C

| | |
|---|---|
| Insulin lispro | 1000 U/ml |
| Sodium phosphate | 2 mM |
| phenol | 15.9 mM |
| m-cresol | 15.9 mM |
| Ionic zinc (as $ZnCl_2$) | 197 μg/ml (3 mM), equals 0.55% (w/w) based on the weight of insulin compound in the composition |
| Citric acid | 44 mM |
| Glycerol | 174 mM |
| Surfactant | Selected from C1, C2 or C3 (see below) |

-continued

| | |
|---|---|
| Water for injection | qs |
| Residual NaCl | Acidification and subsequent neutralisation during preparation results in formation of 2-4 mM NaCl |
| pH adjusted to 7.4 | |
| Example C1: | surfactant = dodecyl maltoside (0.05 mg/ml) |
| Example C2: | surfactant = polysorbate 20 (TWEEN ® 20) (0.05 mg/ml) |
| Example C3: | surfactant = polyethylene glycol (2) dodecyl ether (BRIJ ® L4) (0.05 mg/ml) |

Example D

| | |
|---|---|
| Insulin lispro | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the composition |
| Citric acid | 44 mM |
| Glycerol | 174 mM |
| Surfactant | Selected from D1, D2 or D3 (see below) |
| Water for injection | qs |
| Residual NaCl | Acidification and subsequent neutralisation during preparation results in formation of 2-4 mM NaCl |
| pH adjusted to 7.8 | |

Example D1: surfactant = dodecyl maltoside (0.05 mg/ml)
Example D2: surfactant = polysorbate 20 (TWEEN ® 20) (0.05 mg/ml)
Example D3: surfactant = polyethylene glycol (2) dodecyl ether (BRIJ ® L4) (0.05 mg/ml)

Example E

| | |
|---|---|
| Insulin glulisine | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the composition |
| Citric acid | 44 mM |
| Glycerol | 174 mM |
| Surfactant | Selected from E1, E2 or E3 (see below) |
| Water for injection | qs |
| Residual NaCl | Acidification and subsequent neutralisation during preparation results in formation of 2-4 mM NaCl |
| pH adjusted to 7.4 | |

Example E1: surfactant = dodecyl maltoside (0.05 mg/ml)
Example E2: surfactant = polysorbate 20 (TWEEN ® 20) (0.05 mg/ml)
Example E3: surfactant = polyethylene glycol (2) dodecyl ether (BRIJ ® L4) (0.05 mg/ml)

Example F

| | |
|---|---|
| Insulin glulisine | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the composition |

-continued

| | |
|---|---|
| Citric acid | 44 mM |
| Glycerol | 174 mM |
| Surfactant | Selected from F1, F2 or F3 (see below) |
| Water for injection | qs |
| Residual NaCl | Acidification and subsequent neutralisation during preparation results in formation of 2-4 mM NaCl |
| pH adjusted to 7.8 | |

Example F1: surfactant = dodecyl maltoside (0.05 mg/ml)
Example F2: surfactant = polysorbate 20 (TWEEN ® 20) (0.05 mg/ml)
Example F3: surfactant = polyethylene glycol (2) dodecyl ether (BRIJ ® L4) (0.05 mg/ml)

Example G

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the composition |
| TETA | 5 mM |
| Glycerol | 174 mM |
| Surfactant | Selected from G1, G2 or G3 (see below) |
| Water for injection | qs |
| Residual NaCl | Acidification and subsequent neutralisation during preparation results in formation of 2-4 mM NaCl |
| pH adjusted to 7.4 | |

Example G1: surfactant = dodecyl maltoside (0.05 mg/ml)
Example G2: surfactant = polysorbate 20 (TWEEN ® 20) (0.05 mg/ml)
Example G3: surfactant = polyethylene glycol (2) dodecyl ether (BRIJ ® L4) (0.05 mg/ml)

Example H

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the composition |
| TETA | 5 mM |
| Glycerol | 174 mM |
| Surfactant | Selected from H1, H2 or H3 (see below) |
| Water for injection | qs |
| Residual NaCl | Acidification and subsequent neutralisation during preparation results in formation of 2-4 mM NaCl |
| pH adjusted to 7.8 | |

Example H1: surfactant = dodecyl maltoside (0.05 mg/ml)
Example H2: surfactant = polysorbate 20 (TWEEN ® 20) (0.05 mg/ml)
Example H3: surfactant = polyethylene glycol (2) dodecyl ether (BRIJ ® L4) (0.05 mg/ml)

Example I

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the composition |

-continued

| | |
|---|---|
| DETA | 5 mM |
| Glycerol | 174 mM |
| Surfactant | Selected from I1, I2 or I3 (see below) |
| Water for injection | qs |
| Residual NaCl | Acidification and subsequent neutralisation during preparation results in formation of 2-4 mM NaCl |
| pH adjusted to 7.4 | |

Example I1: surfactant = dodecyl maltoside (0.05 mg/ml)
Example I2: surfactant = polysorbate 20 (TWEEN ® 20) (0.05 mg/ml)
Example I3: surfactant = polyethylene glycol (2) dodecyl ether (BRIJ ® L4) (0.05 mg/ml)

Example J

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 197 µg/ml (3 mM), equals 0.55% (w/w) based on the weight of insulin compound in the composition |
| TETA | 5 mM |
| Glycerol | 174 mM |
| Surfactant | Selected from J1, J2 or J3 (see below) |
| Water for injection | qs |
| Residual NaCl | Acidification and subsequent neutralisation during preparation results in formation of 2-4 mM NaCl |
| pH adjusted to 7.8 | |

Example J1: surfactant = dodecyl maltoside (0.05 mg/ml)
Example J2: surfactant = polysorbate 20 (TWEEN ® 20) (0.05 mg/ml)
Example J3: surfactant = polyethylene glycol (2) dodecyl ether (BRIJ ® L4) (0.05 mg/ml)

Example K

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Citrate | 44 mM |
| Glycerol | 174 mM |
| EDTA | 0.1 mM |
| Surfactant | Selected from K1, K2 or K3 (see below) |
| Water for injection | qs |
| Residual NaCl | Acidification and subsequent neutralisation during preparation results in formation of 2-4 mM NaCl |
| pH adjusted to 7.4 | |

Example K1: surfactant = dodecyl maltoside (0.05 mg/ml)
Example K1: surfactant = polysorbate 20 (Tween ® 20) (0.05 mg/ml)
Example K2: surfactant = polyethylene glycol (2) dodecyl ether (Brij ® L4) (0.05 mg/ml)

Example L

| | |
|---|---|
| Insulin lispro | 1000 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Citrate | 44 mM |
| Glycerol | 174 mM |
| EDTA | 0.1 mM |

-continued

| | |
|---|---|
| Surfactant | Selected from L1, L2 or L3 (see below) |
| Water for injection | qs |
| Residual NaCl | Acidification and subsequent neutralisation during preparation results in formation of 2-4 mM NaCl |
| pH adjusted to 7.4 | |

Example L1: surfactant = dodecyl maltoside (0.05 mg/ml)
Example L1: surfactant = polysorbate 20 (Tween ® 20) (0.05 mg/ml)
Example L2: surfactant = polyethylene glycol (2) dodecyl ether (Brij ® L4) (0.05 mg/ml)

Example M

| | |
|---|---|
| Insulin aspart | 1000 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Citrate | 44 mM |
| Glycerol | 174 mM |
| EDTA | 0.1 mM |
| Surfactant | Selected from M1, M2 or M3 (see below) |
| Water for injection | qs |
| Residual NaCl | Acidification and subsequent neutralisation during preparation results in formation of 2-4 mM NaCl |
| pH adjusted to 7.8 | |

Example M1: surfactant = dodecyl maltoside (0.05 mg/ml)
Example M1: surfactant = polysorbate 20 (Tween ® 20) (0.05 mg/ml)
Example M2: surfactant = polyethylene glycol (2) dodecyl ether (Brij ® L4) (0.05 mg/ml)

Example N

| | |
|---|---|
| Insulin lispro | 1000 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Citrate | 44 mM |
| Glycerol | 174 mM |
| EDTA | 0.1 mM |
| Surfactant | Selected from N1, N2 or N3 (see below) |
| Water for injection | qs |
| Residual NaCl | Acidification and subsequent neutralisation during preparation results in formation of 2-4 mM NaCl |
| pH adjusted to 7.8 | |

Example N1: surfactant = dodecyl maltoside (0.05 mg/ml)
Example N1: surfactant = polysorbate 20 (Tween ® 20) (0.05 mg/ml)
Example N2: surfactant = polyethylene glycol (2) dodecyl ether (Brij ® L4) (0.05 mg/ml)

Example O

| | |
|---|---|
| Insulin compound* | 1000 U/ml |
| Sodium phosphate | 2 mM |
| phenol | 15.9 mM |
| m-cresol | 15.9 mM |
| Ionic zinc (as $ZnCl_2$) | 19.7 µg/ml (0.3 mM), equals 0.55% (w/w) based on the weight of insulin compound in the formulation |
| Nicotinamide | 80 mM |
| NaCl | 70 mM |
| Dodecyl maltoside | 0.05 mM |
| Water for injection | qs |

-continued

| | |
|---|---|
| Residual NaCl | Acidification and subsequent neutralisation during preparation results in formation of 2-4 mM NaCl |
| pH adjusted to 7.4 | |

Example P

| | |
|---|---|
| Insulin compound* | 1000 U/ml |
| Sodium phosphate | 2 mM |
| phenol | 15.9 mM |
| m-cresol | 15.9 mM |
| Ionic zinc (as $ZnCl_2$) | 19.7 μg/ml (0.3 mM), equals 0.55% (w/w) based on the weight of insulin compound in the formulation |
| Nicotinamide | 80 mM |
| NaCl | 70 mM |
| Dodecyl maltoside | 0.05 mM |
| Water for injection | qs |
| Residual NaCl | Acidification and subsequent neutralisation during preparation results in formation of 2-4 mM NaCl |
| pH adjusted to 7.8 | |

Example Q

| | |
|---|---|
| Insulin compound* | 1000 U/ml |
| Sodium phosphate | 2 mM |
| phenol | 15.9 mM |
| m-cresol | 15.9 mM |
| Ionic zinc (as $ZnCl_2$) | 19.7 μg/ml (0.3 mM), equals 0.55% (w/w) based on the weight of insulin compound in the formulation |
| Nicotinamide | 80 mM |
| NaCl | 70 mM |
| Polysorbate 80 | 0.05 mg/ml |
| Water for injection | qs |
| Residual NaCl | Acidification and subsequent neutralisation during preparation results in formation of 2-4 mM NaCl |
| pH adjusted to 7.4 | |

Example R

| | |
|---|---|
| Insulin compound* | 1000 U/ml |
| Sodium phosphate | 2 mM |
| phenol | 15.9 mM |
| m-cresol | 15.9 mM |
| Ionic zinc (as $ZnCl_2$) | 19.7 μg/ml (0.3 mM), equals 0.55% (w/w) based on the weight of insulin compound in the formulation |

-continued

| | |
|---|---|
| Nicotinamide | 80 mM |
| NaCl | 70 mM |
| Polysorbate 20 | 0.05 mg/ml |
| Water for injection | qs |
| Residual NaCl | Acidification and subsequent neutralisation during preparation results in formation of 2-4 mM NaCl |
| pH adjusted to 7.4 | |

Examples O to R: * Insulin compound = insulin aspart or insulin lispro or insulin glulisine or recombinant human insulin Method for Preparation for the Above Compositions:

Insulin powder is added to water and HCl is added until the powder is fully dissolved (pH has to be <3 in order to achieve full dissolution). $ZnCl_2$ is added to the required level. Once dissolved, pH is adjusted to approximately 7 and volume is adjusted with water so that the insulin concentration is 2× the required concentration. The composition is then mixed 1:1 (v/v) with a mixture of additional excipients (all at 2× the required concentration).

Example 2—Effect of Dodecyl Maltoside and Polysorbate 80 on the Stability of Insulin Aspart (1000 U/Ml) in the Presence of Trisodium Citrate, L-Histidine and Pyrophosphate Stability of insulin aspart (1000 U/ml) was investigated in compositions comprising trisodium citrate (44 mM), L-histidine (22 mM) or pyrophosphate (22 mM), both in the presence and in the absence of dodecyl maltoside or polysorbate 80. All compositions (except control based on NOVORAPID® composition, see below) further comprised phenol (15.9 mM), m-cresol (15.9 mM), sodium phosphate (2 mM), glycerol (174 mM), sodium chloride (10 mM) and ionic zinc (197 μg/ml, excluding counter-anion, as $ZnCl_2$) and were adjusted to pH 7.4. For comparison, a composition of insulin aspart (1000 U/ml) in the composition of the 100 U/ml commercial insulin aspart product (NOVORAPID®) was also included in the study. This composition was prepared using the same procedure as that used for all other 1000 U/ml compositions studied in this experiment and contained the excipients of the commercial NOVORAPID® product. The concentration of ionic zinc was adjusted to ensure the ratio between insulin aspart and ionic zinc was the same as that in the 100 U/ml NOVORAPID® product. The composition thus comprised sodium phosphate (7 mM), glycerol (174 mM), sodium chloride (10 mM), phenol (15.9 mM), m-cresol (15.9 mM) and ionic zinc (197 μg/ml, excluding counter-anion) and was adjusted to pH 7.4.

It was shown (Table 1) that the presence of trisodium citrate, L-histidine or pyrophosphate resulted in a considerable increase in the rate of particle formation of insulin aspart, using the Visual Assessment Scoring Method A. The presence of dodecyl maltoside mitigated the destabilising effect. Polysorbate 80 also showed a stabilising effect, although not to the same extent as dodecyl maltoside.

TABLE 1

Visual scores of insulin aspart (1000 U/ml) compositions using Visual Assessment Scoring Method A following storage at indicated temperatures.

| Accelerator | Surfactant | Ionic strength* (mM) | T = 0 weeks | 2-8° C. (12 weeks) | 30° C. (4 weeks) | 30° C. (12 weeks) | 37° C. (4 weeks) |
|---|---|---|---|---|---|---|---|
| None | None | 24.16 | 1 | 1 | 2 | 2 | 3 |
| Citrate (44 mM) | None | 24.16 | 1 | 2 | 4 | 5 | 5 |
| Citrate (44 mM) | Dodecyl maltoside (50 μg/ml) | 24.16 | 1 | 1 | 1 | 2 | 3 |
| Citrate (44 mM) | Polysorbate 80 (50 μg/ml) | 24.16 | 1 | 2 | 1 | 3 | 5 |
| Histidine (22 mM) | None | 24.16 | 1 | 2 | 4 | 5 | 5 |
| Histidine (22 mM) | Dodecyl maltoside (50 μg/ml) | 24.16 | 1 | 1 | 2 | 3 | 4 |
| Histidine (22 mM) | Polysorbate 80 (50 μg/ml) | 24.16 | 1 | 2 | 4 | 5 | 4 |
| Pyrophos-phate (22 mM) | None | 24.16 | 1 | 3 | 5 | 5 | 5 |
| Pyrophos-phate (22 mM) | Dodecyl maltoside (50 μg/ml) | 24.16 | 1 | 1 | 2 | 3 | 4 |
| Pyrophos-phate (22 mM) | Polysorbate 80 (50 μg/ml) | 24.16 | 1 | 1 | 4 | 5 | 5 |
| NOVORAPID ® control (formulated at 1000 U/ml) | | 35.83 | 1 | 1 | 2 | 2 | 3 |

*ionic strength calculation takes into account all ions in the composition except for the zinc binding species (trisodium citrate, L-histidine or pyrophosphate) and the insulin compound using formula I.

Example 3—Effect of NaCl Concentration on the Stability of Insulin Aspart (1000 U/Ml) Both in the Presence and in the Absence of Trisodium Citrate/Dodecyl Maltoside Combination The effect of NaCl concentration on the stability of insulin aspart (1000 U/ml) was investigated both in the presence and in the absence of trisodium citrate (44 mM)/dodecyl maltoside (50 μg/ml) combination. All compositions further comprised phenol (15.9 mM), m-cresol (15.9 mM), sodium phosphate (2 mM), ionic zinc (197 μg/ml, excluding counter-anion, as $ZnCl_2$) and were adjusted to pH 7.4.

The compositions comprised either glycerol (174 mM) or NaCl (150 mM) or a mixture of glycerol and NaCl as a tonicity modifier (See Table 2). The concentration of glycerol in the compositions comprising a mixture of glycerol and NaCl was less than 174 mM so that the overall osmolarity of the compositions remained the same as in the compositions comprising glycerol only.

It was shown (Table 2) that the stability of insulin aspart (1000 U/ml) was negatively impacted by the presence of NaCl, both in the absence and in the presence of trisodium citrate (44 mM)/dodecyl maltoside (50 μg/ml) combination. In the absence of the trisodium citrate (44 mM)/dodecyl maltoside (50 μg/ml) combination, the stability was comparable using glycerol (174 mM) and glycerol (154 mM)/NaCl (10 mM) mixture as a tonicity modifier. However, considerable impairment in stability was observed when 150 mM NaCl was used. Interestingly, the impairment was observed only at 2-8° C. where a marked increase in the rate of particle formation was observed in the presence of 150 mM NaCl. The detrimental impact of increasing NaCl concentration on the stability of insulin aspart (1000 U/ml) was also observed in the presence of trisodium citrate (44 mM)/dodecyl maltoside (50 μg/ml) combination. Whilst only a small difference was observed between compositions comprising glycerol (174 mM) and glycerol (154 mM)/NaCl (10 mM) mixture as tonicity modifiers, a composition comprising glycerol (154 mM)/NaCl (50 mM) mixture showed a considerably impaired stability at 2-8° C.

It was thus demonstrated that increasing the ionic strength of the composition of insulin aspart at 1000 U/ml leads to an increased rate of particle formation.

Interestingly, this effect is not observed at lower concentrations (e.g. 100 U/ml) of insulin aspart, where an increase in the ionic strength of the composition can actually improve the stability of the composition (data not shown). Similarly, for insulin lispro, while maintaining a low ionic strength at 1000 U/ml concentration provides improved stability, this effect is not observed a lower concentrations of insulin lispro (e.g. 100 U/ml) (data not shown).

TABLE 2

Visual scores of insulin aspart (1000 U/ml) compositions using Visual Assessment Scoring Method A following storage at indicated temperatures.

| Citrate | Tonicity modifier | Trisodium citrate (mM)/ Dodecyl maltoside (μg/ml) | Ionic strength* (mM) | T = 0 weeks | 2-8° C. (12 weeks) | 30° C. (4 weeks) | 30° C. (12 weeks) | 37° C. (4 weeks) |
|---|---|---|---|---|---|---|---|---|
| 0 mM | Glycerol (174 mM) | 0/0 | 14.16 | 1 | 1 | 1 | 2 | 3 |
| 0 mM | Glycerol (154 mM) + NaCl (10 mM) | 0/0 | 24.16 | 1 | 1 | 2 | 2 | 3 |
| 0 mM | NaCl (150 mM) | 0/0 | 164.16 | 1 | 5 | 2 | 2 | 2 |
| 44 mM | Glycerol (174 mM) | 44/50 | 14.16 | 1 | 1 | 1 | 2 | 3 |
| 44 mM | Glycerol (154 mM) + NaCl (10 mM) | 44/50 | 24.16 | 1 | 1 | 1 | 2 | 3 |
| 44 mM | Glycerol (74 mM) + NaCl (50 mM) | 44/50 | 64.16 | 1 | 5 | 3 | 3 | 5 |

*ionic strength calculation takes into account all ions in the composition except for the zinc binding species (trisodium citrate) and the insulin compound using formula I.

Example 4: Comparison of the Source of Citrate and the pH of the Composition on the Stability of Insulin Aspart (1000 U/ml)

The effect of the source of citrate anion and the pH of the composition on the stability of insulin aspart (1000 U/ml) was investigated. Citric acid and trisodium citrate were compared as the source of the citrate anion. The composition comprising citric acid was tested at pH 7.8 and the composition comprising trisodium citrate was tested at pH 7.4. Both compositions further comprised phenol (15.9 mM), m-cresol (15.9 mM), sodium phosphate (2 mM), glycerol (174 mM), dodecyl maltoside (50 μg/ml) and ionic zinc (197 μg/ml, excluding counter-anion, as $ZnCl_2$).

It was shown (Table 3) that the source of citrate and the pH had a minimal impact on the stability of insulin aspart. The composition comprising citric acid (pH 7.8) appeared to be very slightly more stable at the 8 week time-point at 30° C.

TABLE 3

Visual scores of insulin aspart (1000 U/ml) compositions using Visual Assessment Scoring Method A following storage at indicated temperatures.

| Source of citrate anion | pH | Ionic strength* (mM) | T = 0 weeks | 2-8° C. (8 weeks) | 30° C. (4 weeks) | 30° C. (8 weeks) | 37° C. (4 weeks) |
|---|---|---|---|---|---|---|---|
| Citric acid (44 mM) | 7.8 | 14.84 | 1 | 1 | 1 | 2 | 3 |
| Trisodium citrate (44 mM) | 7.4 | 14.16 | 1 | 1 | 1 | 3 | 3 |

*ionic strength calculation takes into account all ions in the composition except for the zinc binding species (trisodium citrate, citric acid) and the insulin compound using formula I.

Example 5: Investigation of the Effect of Citric Acid Concentration on the Stability of Insulin Aspart (1000 U/Ml) in the Presence of Dodecyl Maltoside The effect of citric acid concentration on the stability of insulin aspart (1000 U/ml) was investigated in the presence of dodecyl maltoside (0.05 mg/ml). All compositions tested further comprised phenol (15.9 mM), m-cresol (15.9 mM), sodium phosphate (2 mM), glycerol (174 mM), dodecyl maltoside (0.05 mg/ml) and ionic zinc (197 μg/ml, excluding counter-anion, as $ZnCl_2$) and were adjusted to pH 7.8.

It was shown (Table 4) that increasing the concentration of citric acid from 0 to 44 mM had only a very small impact on the stability of insulin aspart (1000 U/ml) in the presence of dodecyl maltoside (0.05 mg/ml). No effect was observed at 2-8° C. and 37° C. for the duration of the experiment, and the rate of particle formation was only very slightly higher in the compositions comprising 22, 33 and 44 mM citric acid compared with compositions comprising 0 and 11 mM citric acid at 30° C.

TABLE 4

Visual scores of insulin aspart (1000 U/ml) compositions using Visual Assessment Scoring Method A following storage at indicated temperatures.

| Citric acid | Ionic strength* (mM) | T = 0 weeks | 2-8° C. (8 weeks) | 30° C. (4 weeks) | 30° C. (8 weeks) | 37° C. (4 weeks) |
|---|---|---|---|---|---|---|
| 0 mM | 14.84 | 1 | 1 | 1 | 1 | 3 |
| 11 mM | 14.84 | 1 | 1 | 1 | 1 | 3 |
| 22 mM | 14.84 | 1 | 1 | 1 | 2 | 3 |
| 33 mM | 14.84 | 1 | 1 | 1 | 2 | 3 |
| 44 mM | 14.84 | 1 | 1 | 1 | 2 | 3 |

*ionic strength calculation takes into account all ions in the composition except for the zinc binding species (citric acid) and the insulin compound using formula I.

Example 6: Investigation of the Optimal Concentration of Dodecyl Maltoside and Polysorbate 80 on the Stability of Insulin Aspart (1000 U/Ml) in the Presence of Different Concentrations of Citric Acid The stability of insulin aspart (1000 U/ml) was investigated in the presence of different concentrations of citric acid and different concentrations of either dodecyl maltoside or polysorbate 80. All compositions tested further comprised phenol (15.9 mM), m-cresol (15.9 mM), sodium phosphate (2 mM), glycerol (174 mM) and ionic zinc (197 μg/ml, excluding counter-anion, as $ZnCl_2$) and were adjusted to pH 7.8. Three concentrations of citric acid (44, 66 and 88 mM) and four concentrations of each non-ionic surfactant were tested as well as corresponding surfactant-free compositions.

The rate of particle formation in compositions of insulin aspart (1000 U/ml) was found to be proportional to citric acid concentration in the range between 44 and 88 mM, with the lower citric acid concentration of 44 mM being most suitable (Table 5). Whilst the presence of both dodecyl maltoside and polysorbate 80 led to a reduction in the rate of particle formation, dodecyl maltoside was found more effective in inhibiting the particle formation than polysorbate 80. The lower concentrations of dodecyl maltoside (0.05 and 0.1 mg/ml) appeared to be more effective in inhibiting the particle formation than higher concentrations (0.2 and 0.3 mg/ml). In contrast, in the case of polysorbate 80 it was the higher concentrations (0.3 and 0.5 mg/ml) that showed a greater ability to reduce the particle formation rate than the lower concentrations (0.05 and 0.1 mg/ml).

TABLE 5

Visual scores of insulin aspart (1000 U/ml) compositions using Visual Assessment Scoring Method A following storage at indicated temperatures.

| Citric acid | Dodecyl maltoside (mg/ml) | Polysorbate 80 (mg/ml) | Ionic strength* (mM) | T = 0 weeks | 2-8° C. (8 weeks) | 30° C. (4 weeks) | 30° C. (8 weeks) | 37° C. (4 weeks) |
|---|---|---|---|---|---|---|---|---|
| 44 mM | 0 | 0 | 14.84 | 1 | 3 | 4 | 5 | 5 |
| 44 mM | 0.05 | 0 | 14.84 | 1 | 1 | 1 | 2 | 3 |
| 44 mM | 0.1 | 0 | 14.84 | 1 | 1 | 1 | 2 | 3 |
| 44 mM | 0.2 | 0 | 14.84 | 1 | 1 | 2 | 2 | 4 |
| 44 mM | 0.3 | 0 | 14.84 | 1 | 2 | 2 | 3 | 5 |
| 44 mM | 0 | 0.05 | 14.84 | 1 | 3 | 2 | 3 | 4 |
| 44 mM | 0 | 0.1 | 14.84 | 1 | 2 | 2 | 3 | 4 |
| 44 mM | 0 | 0.3 | 14.84 | 1 | 2 | 2 | 3 | 4 |
| 44 mM | 0 | 0.5 | 14.84 | 1 | 1 | 1 | 3 | 4 |
| 66 mM | 0 | 0 | 14.84 | 1 | 5 | 5 | 5 | 5 |
| 66 mM | 0.05 | 0 | 14.84 | 1 | 2 | 2 | 4 | 4 |
| 66 mM | 0.1 | 0 | 14.84 | 1 | 3 | 2 | 3 | 4 |
| 66 mM | 0.2 | 0 | 14.84 | 1 | 3 | 2 | 5 | 5 |
| 66 mM | 0.3 | 0 | 14.84 | 1 | 4 | 3 | 5 | 5 |
| 66 mM | 0 | 0.05 | 14.84 | 1 | 5 | 4 | 5 | 5 |
| 66 mM | 0 | 0.1 | 14.84 | 1 | 5 | 4 | 5 | 5 |
| 66 mM | 0 | 0.3 | 14.84 | 1 | 4 | 3 | 4 | 4 |
| 66 mM | 0 | 0.5 | 14.84 | 1 | 4 | 4 | 5 | 5 |
| 88 mM | 0 | 0 | 14.84 | 1 | 5 | 5 | 5 | 5 |
| 88 mM | 0.05 | 0 | 14.84 | 1 | 4 | 2 | 4 | 5 |
| 88 mM | 0.1 | 0 | 14.84 | 1 | 5 | 3 | 3 | 5 |
| 88 mM | 0.2 | 0 | 14.84 | 1 | 5 | 4 | 5 | 5 |
| 88 mM | 0.3 | 0 | 14.84 | 1 | 5 | 4 | 5 | 5 |
| 88 mM | 0 | 0.05 | 14.84 | 1 | 5 | 4 | 5 | 5 |
| 88 mM | 0 | 0.1 | 14.84 | 1 | 5 | 4 | 4 | 5 |
| 88 mM | 0 | 0.3 | 14.84 | 1 | 5 | 3 | 4 | 5 |
| 88 mM | 0 | 0.5 | 14.84 | 1 | 5 | 3 | 5 | 5 |

*ionic strength calculation takes into account all ions in the composition except for the zinc binding species (citric acid) and the insulin compound using formula I.

Example 7—Comparison of Pharmacodynamic and Pharmacokinetic Profiles of Insulin Aspart (100 and 1000 U/Ml) Compositions in the Presence and in the Absence of Citrate and Dodecyl Maltoside Pharmacodynamic and pharmacokinetic profile of insulin aspart was compared in the following compositions using the Diabetic Pig Pharmacokinetic/Pharmacodynamic Model (see General Methods (c)):

Insulin aspart (100 U/ml) in the composition of the currently marketed NOVORAPID® (100 U/ml) rapid-acting product Insulin aspart (1000 U/ml) in the composition of the currently marketed NOVORAPID® (100 U/ml) rapid-acting product Insulin aspart (1000 U/ml) in a composition of the system of the invention comprising 22 mM trisodium citrate and 0.1 mg/ml dodecyl maltoside Insulin aspart (1000 U/ml) in a composition of the system of the invention comprising 44 mM trisodium citrate and 0.1 mg/ml dodecyl maltoside All compositions tested comprised phenol (15.9 mM) and m-cresol (15.9 mM) and were adjusted to pH 7.4. The additional components of each composition are listed in Table 6.

TABLE 6

Additional components in compositions of insulin aspart tested.

| Composition | Insulin aspart (U/ml) | Sodium phosphate (mM) | NaCl (mM) | Glycerol (mM) | Ionic zinc* (μg/ml) | Trisodium citrate (mM) | Dodecyl maltoside (mg/ml) |
|---|---|---|---|---|---|---|---|
| 7A | 100 | 7 | 10 | 174 | 19.7 | | |
| 7B | 1000 | 7 | 10 | 174 | 197 | | |
| 7C | 1000 | 2 | 150 | | 197 | 22 | 0.1 |
| 7D | 1000 | 2 | 150 | | 197 | 44 | 0.1 |

*Does not include the contribution of counter-anion

Pharmacodynamic profiles of compositions 7A-7D are shown in FIG. 1. It was shown that increasing the concentration of insulin aspart from 100 U/ml to 1000 U/ml in the composition of the marketed NOVORAPID® product led to a slower onset of action. This is in line with previous reports of dose-dependent delays of the glucose reduction effect of rapid-acting insulins (e.g. de la Peña et al. Pharmacokinetics and Pharmacodynamics of High-Dose Human Regular U-500 Insulin Versus Human Regular U-100 Insulin in Healthy Obese Subjects, Diabetes Care, 34, pp 2496-2501, 2011). It was also shown (FIG. 1) that a composition of insulin aspart (1000 U/ml) comprising 44 mM trisodium citrate and 0.1 mg/ml dodecyl maltoside resulted in a pharmacodynamic profile that was comparable with that achieved by the composition of the marketed NOVORAPID® product (100 U/ml). Such acceleration of the onset of the glucose reduction was not observed in a composition comprising 22 mM trisodium citrate and 0.1 mg/ml dodecyl maltoside, indicating that this concentration of citrate is too low to achieve the accelerating effect at this concentration of insulin aspart.

The pharmacokinetic profiles of compositions 7A, 7B and 7D (FIG. 2) were in line with the pharmacodynamic profiles, showing that increasing the concentration of insulin aspart from 100 U/ml to 1000 U/ml in the composition of the marketed NOVORAPID® product led to a slower increase in serum insulin level, whereas the composition comprising 44 mM trisodium citrate and 0.1 mg/ml dodecyl maltoside resulted in a profile that was comparable with that achieved by the composition of the marketed NOVORAPID® product (100 U/ml). The pharmacokinetic profile of Composition 7C was not tested.

The $T_{MAX}$ and $T_{1/2\ MAX}$ mean values and standard deviations (SD) relating to the pharmacokinetic profiles of compositions 7A, 7B and 7D are shown in Table 7 below.

TABLE 7

$T_{MAX}$ and $T_{1/2MAX}$ mean values and standard deviations (SD) relating to the pharmacokinetic profiles of compositions 7A, 7B and 7D.

| | $T_{MAX}$ (mean) | $T_{MAX}$ (SD) | $T_{1/2MAX}$ (mean) | $T_{1/2MAX}$ (SD) |
|---|---|---|---|---|
| 7A | 25.71 | 8.38 | 8.01 | 2.35 |
| 7B | 90.83 | 21.68 | 28.67 | 8.02 |
| 7D | 20.71 | 6.07 | 7.00 | 3.53 |

Results of the Student's t-test performed to evaluate bioequivalence between compositions 7A, 7B and 7D are shown in Table 8 below. Composition 7A and 7D were shown to be bioequivalent, whereas compositions 7A and 7B and compositions 7B and 7D were shown to be non-bioequivalent.

TABLE 8

Bioequivalence t-test analysis of the pharmacokinetic profiles of compositions 7A, 7B and 7D.

| | $T_{MAX}$ p-value | $T_{1/2MAX}$ p-value |
|---|---|---|
| 7A vs 7B | 0.0118 | 0.0115 |
| 7A vs 7D | 0.2507 | 0.3762 |
| 7B vs 7D | 0.0177 | 0.0107 |

Example 8—Effect of Surfactants on the Stability of Insulin Aspart (1000 U/Ml) in a Glass Vial Under Agitation Stress The effect of surfactants was investigated on the stability of insulin aspart under agitation stress at 25° C. Formulations of insulin aspart (1000 U/ml) were placed in Type 1 glass vials with bromobutyl rubber stopper. The vials were placed on an orbital shaker and agitated at 110 RPM (25° C.). Stability of the samples was tested using Visual Assessment Scoring Method A. All formulations comprised insulin aspart (1000 U/ml), phenol (15.9 mM), m-cresol (15.9 mM), glycerol (174 mM), ionic zinc (197 μg/ml—excluding counter-anion, as $ZnCl_2$) and sodium phosphate (2 mM) and were adjusted to pH 7.4. Additional ingredients are shown in Table 9.

TABLE 9

| Additional ingredients in formulations (8A-8J) of insulin aspart (1000 U/ml). | | |
|---|---|---|
| Formulation | Sodium citrate (mM) | Surfactant (all at 50 μg/ml) |
| 8A | 0 | None |
| 8B | 0 | Polysorbate 80 |
| 8C | 0 | Poloxamer 188 |
| 8D | 0 | Dodecyl maltoside |
| 8E | 0 | Decyl glucopyranoside |
| 8F | 44 | None |
| 8G | 44 | Polysorbate 80 |
| 8H | 44 | Poloxamer 188 |
| 8I | 44 | Dodecyl maltoside |
| 8J | 44 | Decyl glucopyranoside |

It was shown (Table 10) that the presence of alkyl glycosides, particularly dodecyl maltoside, resulted in a considerably slower rate of particle formation of insulin aspart, both in the presence and in the absence of 22 mM trisodium citrate. Other non-ionic surfactants (polysorbate 80 and poloxamer 188) also showed a stabilising effect, although not to the same extent as the alkyl glycosides.

TABLE 10

| Visual scores of insulin aspart (1000 U/ml) formulations using Visual Assessment Scoring Method A following agitation (110 RPM) at 25° C. | | | | |
|---|---|---|---|---|
| Formulation | 1 day | 2 days | 3 days | 7 days |
| 8A | 4 | 5 | 5 | 5 |
| 8B | 2 | 3 | 4 | 5 |
| 8C | 3 | 4 | 5 | 5 |
| 8D | 1 | 1 | 1 | 2 |
| 8E | 1 | 2 | 3 | 4 |
| 8F | 5 | 5 | 5 | 5 |
| 8G | 2 | 2 | 3 | 5 |
| 8H | 4 | 5 | 5 | 5 |
| 8I | 1 | 1 | 1 | 3 |
| 8J | 1 | 2 | 3 | 3 |

Example 9—Effect of Surfactants on the Stability of Insulin Aspart (1000 U/Ml) in an Infusion Pump Reservoir Under Agitation Stress The effect of surfactants was investigated on the stability of insulin aspart in an infusion pump reservoir under agitation stress at 25° C. 2 mL aliquots of insulin aspart formulations (1000 U/ml) were placed in a 3 mL polypropylene infusion pump reservoir (MMT-332A). The reservoirs were placed on an orbital shaker and agitated at 110 RPM (25° C.). The experiment was designed to mimic the stress experienced during use of a medical infusion pump. Stability of the samples was tested using Visual Assessment Scoring Method A. All formulations comprised insulin aspart (1000 U/ml), phenol (15.9 mM), m-cresol (15.9 mM), glycerol (174 mM), ionic zinc (197 μg/ml—excluding counter-anion, as $ZnCl_2$) and sodium phosphate (2 mM) and were adjusted to pH 7.4. Additional ingredients are shown in Table 11.

TABLE 11

| Additional ingredients in formulations (9A-9J) of insulin aspart (1000 U/ml). | | |
|---|---|---|
| Formulation | Sodium citrate (mM) | Surfactant (all at 50 μg/ml) |
| 9A | 0 | None |
| 9B | 0 | Polysorbate 80 |
| 9C | 0 | Poloxamer 188 |
| 9D | 0 | Dodecyl maltoside |
| 9E | 0 | Decyl glucopyranoside |
| 9F | 44 | None |
| 9G | 44 | Polysorbate 80 |
| 9H | 44 | Poloxamer 188 |
| 9I | 44 | Dodecyl maltoside |
| 9J | 44 | Decyl glucopyranoside |

It was shown (Table 12) that the presence of alkyl glycosides, particularly dodecyl maltoside, resulted in a considerably slower rate of particle formation of insulin aspart, both in the presence and in the absence of 22 mM trisodium citrate. Other non-ionic surfactants (polysorbate 80 and poloxamer 188) also showed a stabilising effect, although not to the same extent as the alkyl glycosides.

TABLE 12

| Visual scores of insulin aspart (1000 U/ml) formulations in a polypropylene infusion pump reservoir, using Visual Assessment Scoring Method A following agitation (110 RPM) at 25° C. | | | | |
|---|---|---|---|---|
| Formulation | 1 day | 2 days | 3 days | 7 days |
| 9A | 2 | 3 | 5 | 5 |
| 9B | 2 | 2 | 2 | 4 |
| 9C | 3 | 3 | 4 | 5 |
| 9D | 1 | 1 | 1 | 2 |
| 9E | 1 | 2 | 2 | 4 |
| 9F | 5 | 5 | 5 | 5 |
| 9G | 2 | 2 | 3 | 5 |
| 9H | 2 | 3 | 4 | 5 |
| 9I | 1 | 1 | 1 | 2 |
| 9J | 1 | 2 | 2 | 3 |

Example 10—Continuous Pumping of Insulin Aspart (1000 U/Ml) Compositions Comprising Dodecyl Maltoside Using an Infusion Pump Formulations of insulin aspart (1000 U/ml) were placed in a 3 mL polypropylene infusion pump reservoir (MMT-332A). The reservoirs were placed in the Minimed Paradigm insulin infusion pump. The content of the reservoir was dispensed by the action of the pump, using 0.25 μL pulse at a frequency of 1 pulse per minute. Visual assessment was performed on the dispensed portion. Two formulations were tested. Both formulations comprised insulin aspart (1000 U/ml), phenol (15.9 mM), m-cresol (15.9 mM), glycerol (174 mM), ionic zinc (197 μg/ml—excluding counter-anion, as $ZnCl_2$) and sodium phosphate (2 mM) and were adjusted to pH 7.4. One formulation further comprised sodium citrate (44 mM). the other formulation did not comprise sodium citrate. Both formulations scored visual score 1 after 5 days of pumping, using Visual Assessment Scoring Method A.

Example 11—Effect of Surfactants on the Stability of Insulin Aspart in a Medical Infusion Pump System Reservoir Under Various Stress Conditions The effect of surfactants on the stability of insulin aspart in a medical infusion pump system reservoir is investigated at 30° C. and 37° C. both with and without agitation. Sample agitation is carried out using an orbital shaker (100 rpm). All compositions are tested under these stress conditions both with and without a headspace (minimum of 0.5 ml). Stability of the samples is tested by size-exclusion chromatography (formation of soluble aggregates) and by Visual Assessment Scoring Method A (formation of visible particulates). The experiment is designed to mimic the stress experienced during the use of a medical infusion pump system. The stability is tested using three different concentrations of insulin—100 U/ml, 500 U/ml and 1000 U/ml. All compositions tested comprise phenol (15.9 mM), m-cresol (15.9 mM), glycerol (300 mM) and sodium phosphate (2 mM) and are adjusted to pH 7.4. Additional ingredients are shown in Table 13. The testing protocol at all stress conditions is shown in Table 14.

TABLE 13

Additional ingredients in compositions (11A-11AQ) of insulin aspart. All compositions comprise phenol (15.9 mM), m-cresol (15.9 mM), glycerol (300 mM) and sodium phosphate (2 mM) and are adjusted to pH 7.4.

| Composition | Insulin aspart (U/ml) | Ionic zinc (μg/ml)* | Surfactant (all at 50 μg/ml) | Citric acid (mM) |
|---|---|---|---|---|
| 11A | 100 | 19.7 | None | 0 |
| 11B | 100 | 19.7 | Polysorbate 80 | 0 |
| 11C | 100 | 19.7 | Polysorbate 20 | 0 |
| 11D | 100 | 19.7 | Poloxamer 188 | 0 |
| 11E | 100 | 19.7 | Dodecyl maltoside | 0 |
| 11F | 100 | 19.7 | Decyl glucopyranoside | 0 |
| 11G | 100 | 19.7 | BRIJ® L4 | 0 |
| 11H | 100 | 19.7 | None | 22 |
| 11I | 100 | 19.7 | Polysorbate 80 | 22 |
| 11J | 100 | 19.7 | Polysorbate 20 | 22 |
| 11K | 100 | 19.7 | Poloxamer 188 | 22 |
| 11L | 100 | 19.7 | Dodecyl maltoside | 22 |
| 11M | 100 | 19.7 | Decyl glucopyranoside | 22 |
| 11N | 100 | 19.7 | BRIJ® L4 | 22 |
| 11O | 500 | 98.5 | None | 0 |
| 11P | 500 | 98.5 | Polysorbate 80 | 0 |
| 11Q | 500 | 98.5 | Polysorbate 20 | 0 |
| 11R | 500 | 98.5 | Poloxamer 188 | 0 |
| 11S | 500 | 98.5 | Dodecyl maltoside | 0 |
| 11T | 500 | 98.5 | Decyl glucopyranoside | 0 |
| 11U | 500 | 98.5 | BRIJ® L4 | 0 |
| 11W | 500 | 98.5 | None | 22 |
| 11X | 500 | 98.5 | Polysorbate 80 | 22 |
| 11Y | 500 | 98.5 | Polysorbate 20 | 22 |
| 11Z | 500 | 98.5 | Poloxamer 188 | 22 |
| 11AA | 500 | 98.5 | Dodecyl maltoside | 22 |
| 11AB | 500 | 98.5 | Decyl glucopyranoside | 22 |
| 11AC | 500 | 98.5 | BRIJ® L4 | 22 |
| 11AD | 1000 | 197.0 | None | 0 |
| 11AE | 1000 | 197.0 | Polysorbate 80 | 0 |
| 11AF | 1000 | 197.0 | Polysorbate 20 | 0 |
| 11AG | 1000 | 197.0 | Poloxamer 188 | 0 |
| 11AH | 1000 | 197.0 | Dodecyl maltoside | 0 |
| 11AI | 1000 | 197.0 | Decyl glucopyranoside | 0 |
| 11AJ | 1000 | 197.0 | BRIJ® L4 | 0 |
| 11AK | 1000 | 197.0 | None | 22 |
| 11AL | 1000 | 197.0 | Polysorbate 80 | 22 |
| 11AM | 1000 | 197.0 | Polysorbate 20 | 22 |
| 11AN | 1000 | 197.0 | Poloxamer 188 | 22 |
| 11A0 | 1000 | 197.0 | Dodecyl maltoside | 22 |
| 11AP | 1000 | 197.0 | Decyl glucopyranoside | 22 |
| 11AQ | 1000 | 197.0 | BRIJ® L4 | 22 |

*excluding counter-anion, as $ZnCl_2$.

TABLE 14

Testing protocol for compositions 8A-8AQ.

| Stress conditions | | | |
|---|---|---|---|
| Temperature (° C.) | Agitation | Headspace | Time-points for testing by SEC and visual assessment (days) |
| 30 | Yes | Yes | 0, 1, 2, 3, 5, 7, 10, 14 |
| 30 | Yes | No | 0, 1, 2, 3, 5, 7, 10, 14 |
| 30 | No | Yes | 0, 1, 2, 3, 5, 7, 10, 14 |
| 30 | No | No | 0, 1, 2, 3, 5, 7, 10, 14 |
| 37 | Yes | Yes | 0, 1, 2, 3, 5, 7, 10, 14 |
| 37 | Yes | No | 0, 1, 2, 3, 5, 7, 10, 14 |
| 37 | No | Yes | 0, 1, 2, 3, 5, 7, 10, 14 |
| 37 | No | No | 0, 1, 2, 3, 5, 7, 10, 14 |

Example 12—Effect of Surfactants on the Stability of Insulin Aspart During a Pumping Action Using a Medical Infusion Pump System The effect of surfactants on the stability of insulin aspart in a medical infusion pump system reservoir is investigated during the pumping action of an insulin pump at 30° C. and 37° C. both with and without agitation. Sample agitation is carried out using an orbital shaker (100 rpm). An insulin composition (either with or without a surfactant) is transferred into the pump system reservoir. The reservoir is then placed in the insulin pump system, the pump system is placed in an incubator (30° C. or 37° C.) and the insulin composition is pumped at a set basal rate for up to 14 days. The insulin composition removed from the reservoir by the pump action is collected in a glass container and analysed at regular intervals using size-exclusion chromatography (formation of soluble aggregates) and by Visual Assessment Scoring Method A (formation of visible particulates). Insulin stability is tested using three different concentrations of insulin—100 U/ml, 500 U/ml and 1000 U/ml. All compositions tested comprise phenol (15.9 mM), m-cresol (15.9 mM), glycerol (300 mM) and sodium phosphate (2 mM) and are adjusted to pH 7.4. Additional ingredients are shown in Table 15. The testing protocol at all stress conditions is shown in Table 16.

TABLE 15

Additional ingredients in compositions (12A-12AQ) of insulin aspart. All compositions comprise phenol (15.9 mM), m-cresol (15.9 mM), glycerol (300 mM) and sodium phosphate (2 mM) and are adjusted to pH 7.4.

| Composition | Insulin aspart (U/ml) | Ionic zinc (μg/ml)* | Surfactant (all at 50 μg/ml) | Citric acid (mM) |
|---|---|---|---|---|
| 12A | 100 | 19.7 | None | 0 |
| 12B | 100 | 19.7 | Polysorbate 80 | 0 |
| 12C | 100 | 19.7 | Polysorbate 20 | 0 |
| 12D | 100 | 19.7 | Poloxamer 188 | 0 |
| 12E | 100 | 19.7 | Dodecyl maltoside | 0 |
| 12F | 100 | 19.7 | Decyl glucopyranoside | 0 |
| 12G | 100 | 19.7 | BRIJ® L4 | 0 |
| 12H | 100 | 19.7 | None | 22 |
| 12I | 100 | 19.7 | Polysorbate 80 | 22 |
| 12J | 100 | 19.7 | Polysorbate 20 | 22 |
| 12K | 100 | 19.7 | Poloxamer 188 | 22 |
| 12L | 100 | 19.7 | Dodecyl maltoside | 22 |
| 12M | 100 | 19.7 | Decyl glucopyranoside | 22 |
| 12N | 100 | 19.7 | BRIJ® L4 | 22 |
| 12O | 500 | 98.5 | None | 0 |

TABLE 15-continued

Additional ingredients in compositions (12A-12AQ) of insulin aspart. All compositions comprise phenol (15.9 mM), m-cresol (15.9 mM), glycerol (300 mM) and sodium phosphate (2 mM) and are adjusted to pH 7.4.

| Composition | Insulin aspart (U/ml) | Ionic zinc (μg/ml)* | Surfactant (all at 50 μg/ml) | Citric acid (mM) |
|---|---|---|---|---|
| 12P | 500 | 98.5 | Polysorbate 80 | 0 |
| 12Q | 500 | 98.5 | Polysorbate 20 | 0 |
| 12R | 500 | 98.5 | Poloxamer 188 | 0 |
| 12S | 500 | 98.5 | Dodecyl maltoside | 0 |
| 12T | 500 | 98.5 | Decyl glucopyranoside | 0 |
| 12U | 500 | 98.5 | BRIJ® L4 | 0 |
| 12W | 500 | 98.5 | None | 22 |
| 12X | 500 | 98.5 | Polysorbate 80 | 22 |
| 12Y | 500 | 98.5 | Polysorbate 20 | 22 |
| 12Z | 500 | 98.5 | Poloxamer 188 | 22 |
| 12AA | 500 | 98.5 | Dodecyl maltoside | 22 |
| 12AB | 500 | 98.5 | Decyl glucopyranoside | 22 |
| 12AC | 500 | 98.5 | BRIJ® L4 | 22 |
| 12AD | 1000 | 197.0 | None | 0 |
| 12AE | 1000 | 197.0 | Polysorbate 80 | 0 |
| 12AF | 1000 | 197.0 | Polysorbate 20 | 0 |
| 12AG | 1000 | 197.0 | Poloxamer 188 | 0 |
| 12AH | 1000 | 197.0 | Dodecyl maltoside | 0 |
| 12AI | 1000 | 197.0 | Decyl glucopyranoside | 0 |
| 12AJ | 1000 | 197.0 | BRIJ® L4 | 0 |
| 12AK | 1000 | 197.0 | None | 22 |
| 12AL | 1000 | 197.0 | Polysorbate 80 | 22 |
| 12AM | 1000 | 197.0 | Polysorbate 20 | 22 |
| 12AN | 1000 | 197.0 | Poloxamer 188 | 22 |
| 12AO | 1000 | 197.0 | Dodecyl maltoside | 22 |
| 12AP | 1000 | 197.0 | Decyl glucopyranoside | 22 |
| 12AQ | 1000 | 197.0 | BRIJ® L4 | 22 |

*excluding counter-anion, as $ZnCl_2$.

TABLE 16

Testing protocol for compositions 9A-9AQ.

| Stress conditions | | Time-points for testing by SEC |
|---|---|---|
| Temperature (° C.) | Agitation | and visual assessment (days) |
| 30 | Yes | 0, 1, 2, 3, 5, 7, 10, 14 |
| 30 | No | 0, 1, 2, 3, 5, 7, 10, 14 |
| 37 | Yes | 0, 1, 2, 3, 5, 7, 10, 14 |
| 37 | No | 0, 1, 2, 3, 5, 7, 10, 14 |

Example 13—Effect of Surfactants on the Stability of Insulin Lispro in a Medical Infusion Pump System Reservoir Under Various Stress Conditions The protocol of Example 11 is repeated using insulin lispro instead of insulin aspart.

Example 14—Effect of Surfactants on the Stability of Insulin Lispro During a Pumping Action Using a Medical Infusion Pump System The protocol of Example 12 is repeated using insulin lispro instead of insulin aspart.

Example 15—a Pulse Accuracy Study

The pulse accuracy of a medical infusion pump system is investigated for three different pulse volumes using 100 U/ml and 1000 U/ml insulin compositions. The accuracy is compared in the presence and in the absence of a non-ionic surfactant. A microgravimetric system comprising a microanalytical balance positioned on a robust low-vibration table is used. The balance is calibrated internally before use and all measurements are performed at room temperature. The infusion pump is positioned outside of the balance and connected to an infusion line leading into the balance compartment. Within the balance the infusion line is fitted with a needle the end of which is submerged into water in a pre-filled glass container. A layer of paraffin is used at the water surface to prevent evaporation. The pump is started at a set number of pulses per hour and the increase in weight of the container is recorded at regular intervals. The interval of weight measurement is smaller than that of the pulse frequency of the pump. Single-pulse accuracy (percentage deviation from expected pulse volume) is then analysed for each discrete pulse delivered over 200 pulses. In addition, an averaged-pulse accuracy over sustained periods is analysed by averaging discrete pulse errors over predetermined observation time-windows. The single-pulse and average-pulse accuracy is compared using 100 U/ml and 1000 U/ml insulin compositions both with and without a non-ionic surfactant.

Throughout the specification and the claims which follow, unless the context requires otherwise, the word ‘comprise’, and variations such as ‘comprises’ and ‘comprising’, will be understood to imply the inclusion of a stated integer, step, group of integers or group of steps but not to the exclusion of any other integer, step, group of integers or group of steps.

The term “and/or” as used in a phrase such as “A and/or B” herein is intended to include both A and B; A or B; A (alone); and B (alone). Likewise, the term “and/or” as used in a phrase such as “A, B, and/or C” is intended to encompass each of the following embodiments: A, B, and C; A, B, or C; A or C; A or B; B or C; A and C; A and B; B and C; A (alone); B (alone); and C (alone).

All publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference.

```
SEQUENCE LISTING
SEQ ID NO: 1:
GIVEQCCTSICSLYQLENYCN

SEQ ID NO: 2:
FVNQHLCGSHLVEALYLVCGERGFFYTPKT

SEQ ID NO: 3:
FVNQHLCGSHLVEALYLVCGERGFFYTKPT

SEQ ID NO: 4:
FVNQHLCGSHLVEALYLVCGERGFFYTDKT

SEQ ID NO: 5:
FVKQHLCGSHLVEALYLVCGERGFFYTPET
```

The invention claimed is:

1. A medical infusion pump system comprising a pump and a reservoir comprising an aqueous liquid pharmaceutical composition, wherein the pump is capable of delivering the pharmaceutical composition to a mammal, wherein the pharmaceutical composition comprises (i) an insulin compound selected from the group consisting of insulin lispro, insulin glulisine, insulin aspart, insulin glargine, and recombinant human insulin, at a concentration of 400 to 1000 U/mL, (ii) ionic zinc at a concentration of 0.05-1%, by weight of zinc based on the weight of the insulin compound in the composition, (iii) an alkyl glycoside at a concentration of 10-200 μg/mL, (iv) citrate at a concentration of 30 to 60 mM (v) and wherein the composition comprises <7 mM chloride ions, and wherein the pump is capable of delivering the pharmaceutical composition in pulses, at a pulse volume of 0.005 to 0.5 μL.

2. A system according to claim 1, wherein the insulin compound is not insulin glargine.

3. The system according to claim 1, wherein the insulin compound is insulin aspart.

4. The system according to claim 1, wherein the insulin compound is not recombinant human insulin.

5. The system according to claim 1, wherein the insulin compound is present at a concentration of 500-1000 U/ml.

6. The system according to claim 1, wherein the ionic zinc is present at a concentration of 0.3 to 0.75% by weight of zinc based on the weight of insulin compound in the composition.

7. The system according to claim 1, wherein the composition has less than 0.05 mM of EDTA and any other zinc binding species having a log K with respect to zinc ion binding of more than 12.3 at 25° C.

8. The system according to claim 1, wherein the source of the citrate is citric acid.

9. The system according to claim 1, which has less than 0.1 mM of zinc binding species having a log K with respect to zinc ion binding of 10-12.3 at 25° C.

10. The system according to claim 1, wherein the alkyl glycoside is selected from the group consisting of dodecyl maltoside, dodecyl glucoside, octyl glucoside, octyl maltoside, decyl glucoside, decyl maltoside, decyl glucopyranoside, tridecyl glucoside, tridecyl maltoside, tetradecyl glucoside, tetradecyl maltoside, hexadecyl glucoside, hexadecyl maltoside, sucrose monooctanoate, sucrose monodecanoate, sucrose monododecanoate, sucrose monotridecanoate, sucrose monotetradecanoate and sucrose monohexadecanoate.

11. The system according to claim 10, wherein the alkyl glycoside is dodecyl maltoside or decyl glucopyranoside.

12. The system according to claim 10, wherein the alkyl glycoside is dodecyl maltoside.

13. The system according to claim 1, wherein the alkyl glycoside is present at a concentration of 20 to 100 μg/ml.

14. The system according to claim 1, wherein the composition further comprises a tonicity modifying agent.

15. The system according to claim 14, wherein the tonicity modifying agent is an uncharged tonicity modifying agent selected from the group consisting of trehalose, mannitol, glycerol and 1,2-propanediol.

16. The system according to claim 15, wherein the uncharged tonicity modifying agent is glycerol.

17. The system according to claim 1, wherein composition comprises <5 mM chloride ions.

18. The system according to claim 1, wherein the ionic strength of the composition is <40 mM, wherein ionic strength is calculated according to the formula I:

$$I = 0.5 \times \sum_{X=1}^{n} c_x z_x^2$$

in which $c_x$ is molar concentration of ion x mol $L^{-1}$, $z_x$ is the absolute value of the charge of ion x and the sum covers all ions represented by n present in the composition, wherein the contribution of the insulin compound and zinc binding species is not taken into consideration for the purposes of the calculation.

19. The system according to claim 1, wherein the composition has an osmolarity of about 200 to about 500 mOsm/L.

20. The system according to claim 1, wherein the pH of the composition is in the range 5.5 to 9.0.

21. The system according to claim 20, wherein the pH of the composition is in the range 7.0 to 7.5; or wherein the pH of the composition is in the range 7.6 to 8.0.

22. The system according to claim 1, wherein the composition comprises a phosphate buffer.

23. The system according to claim 1, wherein the composition further comprises a preservative selected from the group consisting of phenol, m-cresol, chlorocresol, benzyl alcohol, propylparaben, methylparaben, benzalkonium chloride and benzethonium chloride.

24. The system according to claim 1, wherein the composition further comprises nicotinamide; and/or wherein the composition further comprises nicotinic acid or a salt thereof; and/or wherein the composition further comprises treprostinil or a salt thereof.

25. The system according to claim 1, wherein the composition comprises an insulin compound at a concentration of 500 to 1000 U/ml and less than 0.05 mM EDTA and any other zinc binding species having a log K with respect to zinc ion binding of more than 12.3 at 25° C.

26. The system according to claim 25, wherein citrate is present in the composition at a concentration of 40-60 mM.

27. The system according to claim 1, comprising a controller for controlling the dose and frequency of administration of the composition to the mammal.

28. The system according to claim 1, wherein the pump delivers the insulin compound in the composition to the mammal at a set basal rate which is 0.1-20 U/hr.

29. The system according to claim 1, wherein the volume of the pulse is 0.05 to 0.5 μL.

30. The system according to claim 1, wherein the volume of the pulse is 0.005-0.05 μL.

31. The system according to claim 1, wherein each pulse delivers 0.001-1 U of insulin compound.

32. The system according to claim 1, wherein each pulse delivers 0.05-50 ng of non-ionic surfactant.

33. The system according to claim 1, wherein the ratio between the dose of insulin compound delivered in units and the pulse volume in μL is 0.4:1 to 6:1.

34. The system according to claim 1, wherein the pump delivers 10-1000 pulses per hour.

35. The system according to claim 1, wherein the pump delivers the insulin compound in the composition to the mammal in a bolus dose.

36. The system according to claim 35, wherein the bolus dose is 1-100 U.

37. The system according to claim 1, wherein the reservoir has a total volume of 1 to 3 mL.

38. A system according to claim 1, comprising one or more further reservoirs.

39. The system according to claim 38, wherein the one or more further reservoirs comprise an aqueous liquid pharmaceutical composition comprising an insulin compound as active ingredient.

40. The system according to claim 38, wherein the one or more further reservoirs comprise an aqueous liquid pharmaceutical composition comprising an active ingredient which is not an insulin compound.

41. The system according to claim 1, which is an open-loop system or a closed-loop system.

42. The system according to claim 1, wherein the system is worn on the surface of the body.

43. The system according to claim 1, wherein the system is worn on the surface of the body for 1 day or more.

44. The system according to claim 1, which comprises at least one cannula or needle in fluid communication with the pump or the at least one reservoir for subcutaneously infusing the insulin composition into the mammal.

45. The system according to claim 1, wherein the composition is more stable than an identical composition in the absence of non-ionic surfactant during operation of the pump for 3 to 14 days.

46. The system for use according to claim 45, wherein the system administers the composition subcutaneously to the mammal.

47. A method of treatment of diabetes mellitus which comprises administering to a mammal in need thereof an effective amount of an insulin compound containing composition via a pump using a system according to claim 1.

48. The method according to claim 47, wherein the mammal is a human.

* * * * *